(12) United States Patent
Oksanen et al.

(10) Patent No.: US 9,090,914 B2
(45) Date of Patent: *Jul. 28, 2015

(54) EXTRACTION OF NITROGEN FROM ORGANIC MATERIALS THROUGH AMMONIFICATION BY MIXED BACTERIAL POPULATIONS

(71) Applicant: Ductor Oy, Helsinki (FI)

(72) Inventors: Ilona Oksanen, Helsinki (FI); Susanna Kääriäinen, Espoo (FI); Kerttu Koskenniemi, Helsinki (FI); Nina Virolainen, Helsinki (FI); Saara Hernesniemi, Helsinki (FI)

(73) Assignee: DUCTOR OY, Helsinki (FI)

( * ) Notice: Subject to any disclaimer, the term of this patent is extended or adjusted under 35 U.S.C. 154(b) by 0 days.

This patent is subject to a terminal disclaimer.

(21) Appl. No.: 14/066,089

(22) Filed: Oct. 29, 2013

(65) Prior Publication Data

US 2014/0271438 A1    Sep. 18, 2014

Related U.S. Application Data

(60) Provisional application No. 61/789,062, filed on Mar. 15, 2013.

(51) Int. Cl.
| | |
|---|---|
| C12P 3/00 | (2006.01) |
| C12R 1/145 | (2006.01) |
| C12N 1/20 | (2006.01) |
| C12R 1/01 | (2006.01) |

(52) U.S. Cl.
CPC ... *C12P 3/00* (2013.01); *C12N 1/20* (2013.01); *C12R 1/01* (2013.01); *C12R 1/145* (2013.01)

(58) Field of Classification Search
None
See application file for complete search history.

(56) References Cited

U.S. PATENT DOCUMENTS 8,691,551 B1 * 4/2014 Lahtinen et al. ............. 435/243
2011/0126455 A1   6/2011 Shinohara

FOREIGN PATENT DOCUMENTS

| DE | 10 2012 211 781 A1 | 1/2014 |
| DE | 10 2013 212 357 A1 | 1/2014 |
| EP | 2039775 A2 * | 3/2009 |
| WO | WO 2006/119052 A2 | 11/2006 |

OTHER PUBLICATIONS

Paster, Bruce J; et al; "Phylogeny of the Ammonia-Producing Ruminal Bacteria *Peptostreptococcus anaerobius*, *Clostridium sticklandii*, and *Clostridium aminophilum* sp" International Journal of Systematic Bacteriology, 43, 107-110, 1993.*

Yabu, Hironori; et al; "Thermophilic two-stage dry anaerobic digestion of model garbage with ammonia stripping" Journal of Bioscience and Bioengineering, 111, 312-319, 2011.*

Hernandez-Eugenio, Guadalupe; et al; "*Sporanaerobacter acetigenes* gen. nov., sp. nov., a novel acetogenic, facultatively sulfur-reducing" International Journal of Systematic and Evolutionary Microbiology, 52, 1217-1223, 2002.*

Chen, G.J., Russell, J.B. 1989. More monensin-sensitive, ammonia-producing bacteria from the rumen. *Appl. Environ. Microbiol.* 55, 1052-1057.

Dowd, S.E., Wolcott, R.D., Sun, Y., McKeehan, T., Smith, E., Rhoads, D. 2008a. Polymicrobial nature of chronic diabetic foot ulcer biofilm infections determined using bacterial tag encoded FLX amplicon pyrosequencing (bTEFAP). *PLoS ONE* 3(10): e3326.

Dowd, S.E., Sun. Y., Secor, P.R. Rhoads, D,D., Wolcott, B.M., James, G.A., Wolcott, R.D. 2008b. Survey of bacterial diversity in chronic wounds using Pyrosequencing, DGGE, and full ribosome shotgun sequencing, *BMC Microbiology* 8: 43.

EC. 2009, Regulation (EC) No. 1069/2009 of the European Parliament and of the Council of Oct. 21, 2009 laying down health rules as regards animal by-products and derived products not intended for human consumption and repealing Regulation (EC) No. 1774/2002 (Animal by-products Regulation). *Off.J. Eur. Union* L300: 1-33.

Eschenlauer, S.C.P., McKain, N. Walker, N.D., McEwan, N.R., Newbold, C.J., Wallace, R.J. 2002. Ammonia production by ruminal microorganisms and enumeratin, isolation, and characterization of bacteria capable of growth on peptides and amino acids from the sheep rumen. *Appl. Environ. Microbiol.* 68(10): 4925-4931.

EU. 2011. Commission regulation (EU) No. 142/2011 of Feb. 25, 2011 implementing Regulation (EC) No. 1069/2009 of the European Parliament and of the Council laying down health rules as regards animal by-products and derived products not intended for human consumption and implementing Council Directive 97/78/EC as regards certain samples and items exempt from veterinary checks at the border under that Directive. *Off.J. Eur. Union* L54: 1-354.

Fouts, D.E., Szpakowski, S., Purushe, J., Torralba, M., Waterman, R.C., MacNeil, M.D., Alexander, L.J., Nelson, K.E. 2012. Next generation sequencing to define prokaryotic and fungal diversity in the bovine rumen. *PLoS One* 7(11): e48289.

Krause, D.O., Russell, J.B. 1996. An rRNA approach for assessing the role of obligate amino acid-fermenting bacteria in ruminal amino acid deamination. *Appl. Environ. Microbiol.* 62, 815-821.

Russell, J.B., Strobel, H.J., Chen, G.J. 1988. Enrichment and isolation of a ruminal bacterium with a very high specific activity of ammonia production. *Appl. Environ. Microbiol.* 54, 872-877.

(Continued)

*Primary Examiner* — Blaine Lankford
*Assistant Examiner* — David Berke-Schlessel
(74) *Attorney, Agent, or Firm* — Lucas & Mercanti LLP; Robert P. Michal

(57) ABSTRACT

The invention provides a process for producing ammonia or ammonium from an organic material by fermenting a medium comprising organic material in the presence of a mixed bacterial population capable of ammonification, wherein the fermenting is under conditions, and for a sufficient period of time, to produce a fermentation product that comprises ammonia or ammonium. The organic material includes nitrogenous compounds suitable for conversion to ammonia or ammonium.

12 Claims, 9 Drawing Sheets

(56) References Cited

OTHER PUBLICATIONS

Wolcott, R., Gontcharova, V., Sun, Y., Dowd, S.E. 2009, Evaluation of the bacterial diversity among and within individual venous leg ulcers using bacterial tag-encoded FLX and Titanium amplicon pyrosequencing and metagenomic approaches. *BMC Microbiology* 9: 226.

Nakashimada et al, "Ammonia-Methane two-stage anaerobic digestion of dehydrated waste-activated sludge," Applied Microbiology and Biotechnology, vol. 79. No. 6, May 20, 2008, pp. 1061-1069, XP019623654.

Zeng et al., "Ammonia recovery from anaerobically digested cattle manure by steam stripping" Water Science & Technology, vol. 54, No. 8, Aug. 1, 2006, p. 137-145, XP055123390.

Reich et al., "Enhancement options for the utilization of nitrogen rich animal by-products in anaerobic digestion," Bioresource Technology, Elsevier Bv. GB, vol. 102, No. 3, Feb. 1, 2011, pp. 2503-2510. XP027582877.

Dott et al., "Comparison of autochthonous bacteria nad commercially available cultures with respect to their effectiveness in fuel oil degradation," Journal of Industrial Microbiology, vol. 4, No. 5, 1989, pp. 365-374, XP008169913.

Hernandez-Eugenio et al., "Sporanaerobacter acetigenes gen. nov., sp. nous, a novel acetogenic, facultatively sulfur-reducing bacterium," International Journal of Systematic and Evolutionary microbiology, vol. 52, No. 4, Jul. 1, 2002, pp. 1217-1223, XP055123612.

Ductor Corp., "Ductor Corp. gets R&D funding for research and development to biologically produce ammonia and phosphates— World's first 100% organic method to replace chmical fertilizers and secure global food supply," Internet citation, Jan. 28, 2013, XP002725135 (1 page).

PCT International Search Report and Written Opinion mailed Jun. 30, 2014 and issued by International Searching Authority of European Patent Office in a related PCT International Application No. PCT/IB2014/059539 (17 pages).

\* cited by examiner

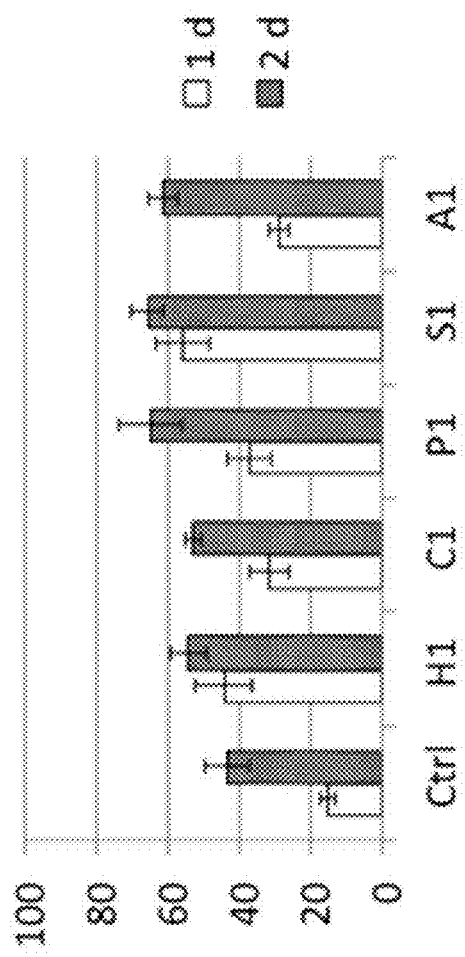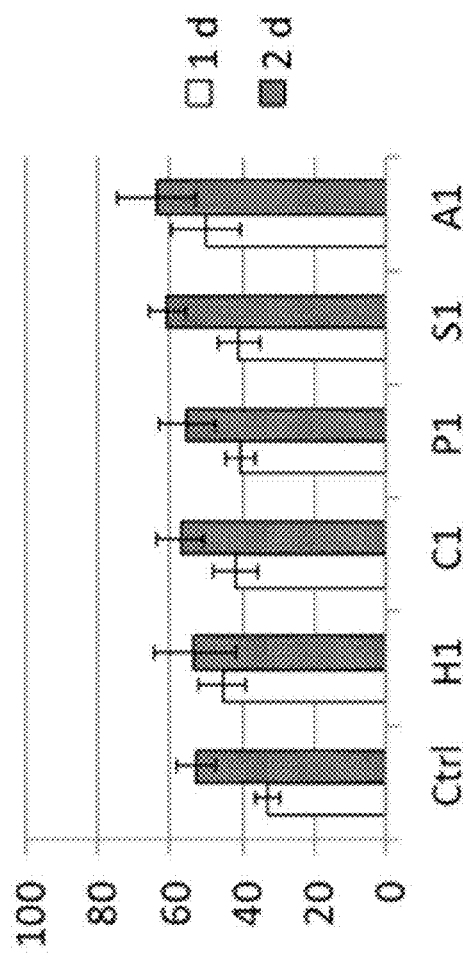

EXTRACTION OF NITROGEN FROM ORGANIC MATERIALS THROUGH AMMONIFICATION BY MIXED BACTERIAL POPULATIONS

TECHNICAL FIELD

The present disclosure relates generally to a new process for producing ammonia and/or ammonium from organic raw materials by a process of microbial fermentation or culture using mixed population of microbes.

BACKGROUND OF THE INVENTION

Ammonia ($NH_3$) is one of the most produced chemical compounds in the world. The global production reached 131M metric tons in 2010 (US Geological Survey 2012). Most of the produced ammonia is used in chemical fertilizers to provide the nitrogen crops need for growing. Ammonia has also been used to produce plastics, synthetic fibers and resins, explosives, and numerous other chemical compounds.

The nitrogen cycle is a process that converts nitrogen between its different chemical forms. Mineralization of nitrogen in organic macromolecules, i.e. conversion of organic nitrogen to ammonium or ammonia, is called ammonification. The release of organic nitrogen as ammonia is a part of the nitrogen cycle, and is performed by ammonifying bacteria.

Ammonification can be utilized to release nitrogen from organic waste materials. For example, U.S. patent application Ser. No. 13/722,228, incorporated by reference herein in its entirety, discloses a method of ammonification. In the method of the '228 application, organic material present in a medium is contacted with a hydrolytic enzyme to produce a medium comprising hydrolyzed or partially hydrolyzed organic material suitable for microbial fermentation or culture. The fermentation is conducted in the presence of at least one microorganism capable of ammonification. The microorganism can belong, for example, to the genus of *Aeromonas, Citrobacter, Clostridium* and *Entrococcus*. The method provided ammonium production rates of up to about 800 mg/liter.

US patent application Publ. No. US20110126455 describes a method for producing an inoculum, which can be used in the mineralization process for producing hydroponics. The inoculum created in the process is able to produce nitrate ion concentrations of up to 400 mg/l and the time required to complete mineralization process is typically 4-8 days.

Thus, there remains a longstanding need in the art for further economical methods for producing ammonia from organic material, e.g., organic waste material.

SUMMARY OF THE INVENTION

Accordingly, there is provided a process for producing ammonia or ammonium from an organic material, the process including the steps of:

fermenting, under aerobic or anaerobic conditions, an aqueous medium including organic material in the presence of a mixed bacterial population capable of ammonification, wherein the fermenting is under conditions, and for a sufficient period of time, to produce a fermentation product that comprises ammonia or ammonium;

wherein the organic material includes nitrogenous compounds suitable for conversion to ammonia or ammonium. Preferably, the nitrogenous compounds are amines or proteins.

In certain embodiments of the invention, the process is conducted at a temperature ranging between 30-60 degrees of Celsius. More preferably, the process is conducted at a temperature ranging from 40-55 degrees Celsius, or from 40-50 degrees of Celsius.

In certain embodiments of the invention, the process is conducted at a pH ranging from about 5 to about 11. More preferably, the process is conducted at a pH ranging from about 6 to about 9.

In certain embodiments of the invention, the fermentation process can be conducted under anaerobic or aerobic conditions in a suitable reaction chamber or vessel for a time period and in a temperature range effective for efficient reduction of the organic material.

Preferably, the process is conducted with a mixed bacterial population that includes a mixed bacterial population substantially similar to a mixed bacterial population selected from the group consisting of H1, C1, P1, S1, A1, PB-M, MF-M, FO1 and FI1. The substantially similar mixed bacterial population preferably has a correlation coefficient of 0.80, more preferably a correlation coefficient of 0.90, and even more preferably a correlation coefficient of 0.95, relative to a mixed bacterial population selected from the group consisting of H1, C1, P1, S1, A1, PB-M, MF-M, FO1 and FI1.

In certain embodiments, the mixed bacterial population is substantially similar to the mixed bacterial population of S1 (CBS Accession No. 136063). The mixed bacterial population substantially similar to S1 preferably has a correlation coefficient of 0.80, more preferably a correlation coefficient of 0.90, and even more preferably a correlation coefficient of 0.95, relative to the mixed bacterial population of S1.

In alternative embodiments, at least half of the cells in the mixed bacterial population comprise of *Sporanaerobacter acetigenes* and/or *Clostridium* spp.

In another embodiment, the mixed bacterial population includes 50-95% *Sporanaerobacter acetigenes* and 3-35% *Clostridium* spp. The cumulative amount of *Sporanaerobacter acetigenes* and/or *Clostridium* spp is 70% or more. Preferably, the mixed bacterial population includes from 50-90% *Sporanaerobacter acetigenes* and 5-15% *Clostridium* spp.

In a further embodiment, the cumulative amount of *Sporanaerobacter acetigenes* and/or *Clostridium* spp is 85% or more. In an additional embodiment, the mixed bacterial population comprises at least 90% bacteria belonging to the order Clostridiales.

Preferably, the inventive process further includes recovering ammonia or ammonium, either mechanically or by precipitation, from the fermentation product. The ammonia or ammonium is optionally recovered by the steps of:

(a) separating solid and liquid fermentation products;

(b) collecting the liquid fermentation product comprising ammonia or ammonium-water or collecting a gas mixture released during the fermenting process or during separating step (a); and (c) recovering the ammonia or ammonium.

In the process according to the invention, the organic material is preferably one or more of the following: meat-and bone meal (MBM), animal meals, animal by-products, slaughterhouse waste, whey, municipal waste, food and fermentation industry waste streams and combinations thereof. The food industry waste streams are, for example, animal by-products, animal meals and food waste.

In a still further embodiment, the invention includes a mixed bacterial population substantially similar to a mixed bacterial population selected from the group consisting of H1, C1, P1, S1, A1, PB-M, MF-M, FO1 and FI1. Preferably, the mixed bacterial population is substantially similar to the mixed bacterial population of S1.

BRIEF DESCRIPTION OF THE DRAWINGS

FIGS. 3A, 3B, 3C, 3D, 3E, 3F, 3G and 3H illustrate the ammonification efficiency of different organic materials by mixed bacterial populations H1, C1, P1, S1, and A1 in Example 2. The error bars indicate the standard deviation between two biological replicates with three technical replicates in each. The organic materials are FIG. 3A: Fish by-product, FIG. 3B: Broiler by-product, FIG. 3C: Bovine/porcine by-product, FIG. 3D: Bioethanol mask, FIG. 3E: Meat-and-bone meal 1, FIG. 3F: Meat-and-bone meal 2, FIG. 3G: Fish meal, FIG. 3H: Feather meal. The results are presented as the percentage of nitrogen converted to ammonia, i.e. ammonification efficiency after incubation at 50° C. for various periods of time. Population S1 stands out as it efficiently ammonifies materials shown by FIGS. 3D and 3G, whereas H1 rapidly ammonifies materials shown by FIGS. 3C, 3D and 3E. In summary, all five populations increase the ammonification efficiency compared to non-inoculated controls. This effect is especially evident in materials shown by FIGS. 3C, 3D, 3E, and 3F. "d" indicates day.

DETAILED DESCRIPTION OF THE INVENTION

Figure 1:
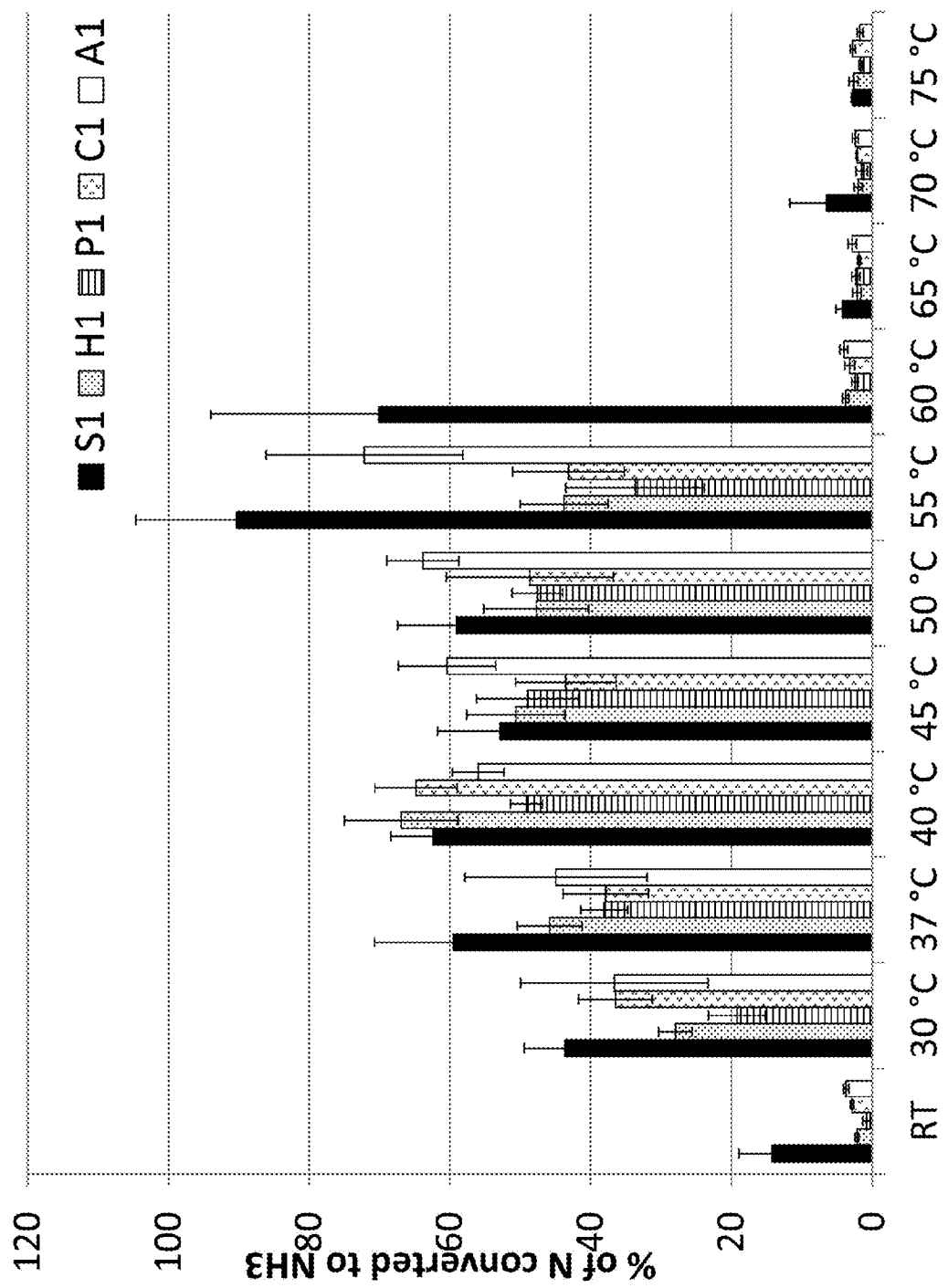
FIG. 1 illustrates determination of the optimum temperature range for the ammonification of meat-and-bone meal ("MBM") proteinacious nitrogen by mixed bacterial populations A1, C1, H1, P1 and S1 in Example 1. The results are presented as the percentage of nitrogen converted to ammonia, i.e. ammonification efficiency after 7 days of incubation at various temperatures. Error bars indicate standard deviation between two biological replicates. The optimal temperature range for ammonification by A1, C1, H1 and P1 is 37-55° C., and for S1 37-60° C. "RT" indicates room temperature.

A method for extraction of nitrogen from organic materials through ammonification by mixed bacterial populations is provided. An organic material can be any protein-rich organic material e.g., of animal or plant origin. In order to more clearly appreciate the invention, the following terms are defined. The terms listed below, unless otherwise indicated, will be used and are intended to be defined as indicated. Definitions for other terms can occur throughout the specification. It is intended that all singular terms also encompass the plural, active tense and past tense forms of a term, unless otherwise indicated.

The term "nitrogenous compounds" refers to nitrogen compounds suitable for conversion to ammonia or ammonium by the process of the invention, e.g., organic nitrogen, including amines, proteins and the like. Examples of such organic material include amine containing material, e.g., proteinacious material such as, e.g., meat-and bone meal (MBM), slaughterhouse waste, whey, municipal waste, fish meal, food industry waste streams, e.g., animal and plant by-products including, but not limited to, the meal of meat-and-bone, fish, and feathers, as well as beet root, legumes, fruit, and sugar industry waste. The term "MBM" "meat-and-bone meal" as employed herein as defined by European Union Commission Regulation No. 142/2011 "meat-and-bone meal means animal protein derived from the processing of Category 1 or Category 2 materials in accordance with one of the processing methods set out in Chapter III of Annex IV".

The term "animal meal" as employed herein is a meal produced from animal materials (such as slaughterhouse waste). In the Examples hereinbelow, "animal meal" was a powder-like material. One process of manufacturing the meal is to take slaughterhouse waste and extract moisture (i.e., dry it) and then mill the dried solids.

The "plant-derived materials" are defined as follows. "Bioethanol mask" (St1 Oy, Finland) refers to fermentation waste originating from bioethanol production. "Barley briquette" (Senson Oy, Finland) was a by-product of wort production, and "Barley mask" (Senson Oy, Finland) was a by-product of barley enzyme production. "Wheat briquette" (CropEnergies AG, Germany) and "Rape cake" (Mildola Oy, Finland) were materials produced to be fed to animals.

The term "animal feed" as used herein describes food prepared for feeding to animals.

The terms "fermenting" or "fermentation" refer to a process where organic molecules serve as both electron donors and acceptors. It differs from respiration, where electrons derived from nutrient molecules are donated to oxygen (aerobic respiration) or other inorganic molecules/ions such as nitrate, sulfate, carbon dioxide or ferric iron (anaerobic respiration). In fermentation, nutrient molecules are reduced to small organic molecules such as volatile fatty acids and alcohols. In addition to this, the term fermentation is used to describe microbial growth on a growth medium within a closed vessel, i.e. bioreactor or fermentor.

The term "ammonia" refers to the compound $NH_3$ found in gaseous form or dissolved in a non-ionized form in a medium e.g., an aqueous medium. The term "ammonium" refers to the ion $NH_4^+$ that is the ionic form of $NH_3$ found in e.g., aqueous solution. In aqueous solution, ammonium and ammonia occur in an equilibrium that is dependent on temperature and pH, e.g. the higher the temperature and the pH, the greater the proportion that is in the form of ammonia. For this reason, reference to "ammonia" herein with regard to the inventive process and/or ammonification microorganisms and products thereof should be understood to include reference to both $NH_3$ and $NH_4^+$ forms of this compound, unless otherwise indicated. For example, discussion of ammonification microorganisms as "ammonia producing" or "ammonium producing" is understood to include production of $NH_3$ and/or $NH_4^+$ according to the $NH_3/NH_4^+$ equilibrium found in the particular medium.

The term ammonification refers to mineralization of nitrogen in organic macromolecules, i.e. conversion of organic nitrogen to ammonium or ammonia. It is performed by ammonifying bacteria and consists of enzymatic hydrolysis of proteins to amino acids, and release of nitrogen as ammonium/ammonia through deamination and elimination reactions. Carbon backbones of amino acids are fermented to organic acids with simultaneous release of carbon dioxide and hydrogen.

The term "unified form," as may be used herein in the context of recovery of ammonium and ammonia from the fermentation or culture products, refers to conversion of ammonium ions into another chemical form such as nonionic ammonia ($NH_3$) and/or any art known nitrogen containing compound, e.g., a compound which is formed by ammonia reacting with nitric acid, sulfuric acid, hydrochloric acid, or phosphoric acid, or some other compound, respectively.

The ammonifying mixed bacterial populations include populations H1, C1, P1, S1, A1, PB-M, MF-M, FO1 and FI1 and variations thereon, and they are described hereinbelow in detail.

Bacterial community analysis of mixed populations H1, C1, P1, S1, and A1 was performed on DNA obtained by phenol-chloroform-isoamyl alcohol extraction from bacterial cultures where cells had been disrupted by bead beating. Populations had been cultured for four days at 37° C., 50° C. or 55° C. in sterile MBM medium [180 g meat-and-bone meal (MBM) per liter of water] or animal-origin materials. Bacterial 16S gene assay by tag-encoded FLX amplicon pyrosequencing (bTEFAP) and bacterial diversity data analysis were performed by the Research and Testing Lab (Lubbock, Tex., USA) as described by Dowd et al. 2008a and Wolcott et al. 2009. Primers 28F 'GAGTTTGATCNTGGCTCAG' (SEQ ID NO: 1) and 519R 'GTNTTACNGCGGCKGCTG' (SEQ ID NO: 2) were used for amplification of 16S variable regions V1-3 (wherein "N" is A, T/U, G or C) and wherein K is T/U or G).

Bacterial diversity analysis revealed the presence of bacteria belonging to 35 different genera (Table 1). Of the total of 53 results, 33 were identified at the species level and 20 at the genus level. TABLE 2 presents the predominant bacterial genera and species in each population. Bacteria belonging to 6-8 genera form the majority of all populations. *Clostridium* spp. and *Sporanaerobacter acetigenes* are predominant in all populations. In S1 cultured at 55° C., *Caloramator* spp. is as common as *Clostridium* spp.

Correlation coefficients (TABLE 3) were calculated from data presented in TABLE 1 using equation [1], where X and Y refer to two matrices, e.g. H1 and C1, between which the correlation is calculated, x and y are single values within a matrix, and $\bar{x}$ and $\bar{y}$ are the means of all values within a matrix. Species not present in the population (empty cells in TABLE 1) were assigned a value 0.

$$\mathrm{Correl}(X, Y) = \frac{\Sigma(x - \bar{x})(y - \bar{y})}{\sqrt{\Sigma(x - \bar{x})^2 \Sigma(y - \bar{y})^2}} \quad [1]$$

The term "substantially similar" with respect to a bacterial population as disclosed herein, means that a bacterial population has a correlation coefficient of at least 0.8 when compared to one or more of the bacterial populations defined by TABLE 1. Preferably, a substantially similar bacterial population has a correlation coefficient of at least 0.9, and more preferably, a substantially similar bacterial population has a correlation coefficient of at least 0.95 when compared to one or more of the bacterial populations defined by TABLE 1. Other statistical methods for comparing populations can be used as well.

TABLE 3 shows a very high similarity between all populations at the age of 4 days. The majority of all populations comprises of only a few species and genera, remaining very similar under all conditions tested and outcompeting innate populations present in animal-origin materials. P1 is the eight generation of a population created from non-sterile MBM, and shows the main characteristics of the population are retained.

Bacterial diversity analyses based on sequencing molecular methods are biased due to e.g. primer specificity and universality (Dowd et al. 2008b). Therefore, the method described hereinabove must be used as a standard when comparisons to the mixed populations presented hereinbelow are performed.

TABLE 1

Bacterial diversity analysis results: genera and species in populations H1, C1, P1, S1, and A1. S1 population was also cultured at 37° C. (marked as S1-37), 50° C. (marked as S1-50, a biological replicate of S1) and 55° C. (marked as S1-55). S1 was also used to inoculate 20% (weight/volume) chicken by-product (CBP), crushed porcine and bovine bone (CB), fish by-product (MF), porcine-bovine by-product (PB) and chicken feathers (FE). Cells from all cultures were harvested for DNA extraction at the age of four days. The results are expressed as percentage of total population.

| Species | A1 | C1 | H1 | P1 | S1 | S1-37 | S1-50 | S1-55 | CBP | CB | MF | PB | FE |
|---|---|---|---|---|---|---|---|---|---|---|---|---|---|
| *Bacillus* sp. | 0.770 | 0.530 | 1.463 | 0.974 | 0.398 | | 0.763 | 1.183 | 0.105 | 2.203 | | 0.127 | 0.031 |
| *Bacillus thermoamylovorans* | 0.224 | 0.106 | 0.506 | 0.394 | 0.085 | | | 0.117 | | 0.283 | | 0.049 | 0.016 |
| *Butyrivibrio fibrisolvens* | | 0.021 | | | | | | | | | | | |
| *Caldicoprobacter oshimai* | 0.050 | 0.042 | 0.113 | 0.021 | 0.085 | 0.035 | 0.111 | 0.105 | | 0.030 | 0.021 | | |
| *Caloramator fervidus* | | | | 0.021 | | | | | | | | | |
| *Caloramator* sp | 5.045 | 2.669 | 4.295 | 4.042 | 5.200 | 5.765 | 3.608 | 3.351 | 0.126 | 3.378 | 1.623 | 3.176 | 1.369 |
| *Carnobacterium divergens* | | | | | | | | | 0.021 | 0.015 | | | |
| *Catabacter* sp | | | | 0.021 | | | 0.012 | | | 0.030 | | 0.019 | |
| *Clostridium botulinum* | | 6.948 | | 6.613 | 4.632 | 1.415 | 4.913 | 0.129 | 1.130 | 1.429 | 1.173 | 6.234 | 0.252 |
| *Clostridium cochlearium* | 5.790 | 6.439 | 6.920 | 11.84 | 8.497 | 10.98 | 2.054 | 0.023 | 2.888 | 5.983 | 2.933 | 2.162 | 0.960 |
| *Clostridium gasigenes* | | | | | | | | | | 0.015 | | |

TABLE 1-continued

Bacterial diversity analysis results: genera and species in populations H1,
C1, P1, S1, and A1. S1 population was also cultured at 37° C. (marked as S1-37), 50° C.
(marked as S1-50, a biological replicate of S1) and 55° C. (marked as S1-55). S1
was also used to inoculate 20% (weight/volume) chicken by-product (CBP), crushed
porcine and bovine bone (CB), fish by-product (MF), porcine-bovine by-product (PB)
and chicken feathers (FE). Cells from all cultures were harvested for DNA extraction
at the age of four days. The results are expressed as percentage of total population.

| Species | A1 | C1 | H1 | P1 | S1 | S1-37 | S1-50 | S1-55 | CBP | CB | MF | PB | FE |
|---|---|---|---|---|---|---|---|---|---|---|---|---|---|
| *Clostridium haemolyticum* | | 0.064 | | | | | 0.014 | | 0.063 | | | | |
| *Clostridium novyi* | | | | | | | | | 0.084 | | | | |
| *Clostridium oceanicum* | | 0.064 | | 0.021 | 0.057 | | 0.014 | | | | | 0.029 | |
| *Clostridium perfringens* | | | | | | | | | | | | 0.136 | |
| *Clostridium* sp | 0.224 | 0.487 | 0.619 | 0.124 | 0.568 | 0.069 | 0.569 | 1.242 | 0.419 | 0.506 | 0.168 | 0.672 | 0.283 |
| *Clostridium sporogenes* | 0.547 | 0.530 | 1.182 | 0.187 | 0.483 | 0.380 | 2.304 | 0.305 | 3.035 | 1.667 | 0.220 | 4.120 | 0.031 |
| *Clostridium thermopalmarium* | | | | | | | | 0.012 | | | | | |
| *Clostridium ultunense* | 2.584 | 5.507 | 0.844 | 15.17 | 1.250 | 1.105 | 0.999 | 1.464 | 0.230 | 0.893 | 1.917 | 0.224 | 2.202 |
| *Corynebacterium kroppenstedtii* | | | | | | | | | | 0.015 | | | |
| *Corynebacterium pseudogenitalium* | | | | | | | | | | 0.015 | | | 0.016 |
| *Cyanobacterium* sp | | | | | | | | | | | | | 0.016 |
| *Enterococcus faecalis* | | | | | | | | | | | | | 0.079 |
| *Enterococcus* sp | | | | | | | | | | | | | 0.063 |
| *Faecalibacterium* sp | | 0.019 | | | | | 0.035 | | | | | 0.049 | |
| *Fervidicola ferrireducens* | | | | 0.021 | | | 0.014 | | | | | | |
| *Garciella* sp | 0.075 | 0.085 | 0.038 | 0.083 | 0.028 | 0.069 | 0.056 | 0.012 | | 0.060 | 0.021 | 0.058 | |
| *Geobacter grbiciae* | | | | | | | | | | | | 0.010 | |
| *Kocuria* sp | | | | | | 0.035 | | | | | | | |
| *Lactobacillus crispatus* | | | | 0.041 | | | | | | | | | |
| *Lactobacillus johnsonii* | | | | | | | | | | | | | 0.047 |
| *Leptospira broomii* | | 0.021 | | | | | | | | | | | |
| *Macrococcus caseolyticus* | | | | | | | | | | | | | 1.935 |
| *Mahella australiensis* | 0.547 | 0.360 | 0.338 | 0.352 | 0.426 | 0.483 | 0.500 | 0.340 | | 0.402 | 0.115 | 0.273 | 0.173 |
| *Microbacterium aurum* | | 0.021 | | | | | | | | | | | |
| *Mycobacterium phocaicum* | | | | | | | | | | | | | 0.016 |
| *Propionibacterium acnes* | | | | | | | | | 0.012 | 0.021 | | 0.010 | |
| *Propionibacterium* sp | | | | | 0.028 | | | | | | | | |
| *Pseudobutyrivibrio ruminis* | | | | | 0.028 | | | | | 0.015 | | | |
| *Pseudomonas* sp | | | | | | | | | | | | | |
| *Rhodobacter* sp | | | | | | | | | | | | 0.019 | |
| *Ruminococcus* sp | | | | | | | 0.014 | | | | | | 0.016 |
| *Sarcina* sp | | | | | | | | | | | | | 0.016 |
| *Sphingomonas mucosissima* | | 0.021 | | | | | | | | | | | |
| *Sporanaerobacter acetigenes* | 77.44 | 74.26 | 80.66 | 53.67 | 75.87 | 78.63 | 81.96 | 85.45 | 90.62 | 81.08 | 90.80 | 81.17 | 92.24 |
| *Sporichthya* sp | | | | | | 0.035 | | | | | | | |
| *Subdoligranulum* sp | | | | | | | | | | | | 0.010 | |
| *Tepidanaerobacter* sp | 2.261 | 1.419 | 1.219 | 4.167 | 0.682 | | 0.791 | 5.319 | 0.837 | 0.253 | 0.429 | 0.438 | |
| *Thermosediminibacter* sp | | | | | | | | | | | | 0.010 | |
| *Tissierella creatinophila* | | 0.021 | | | | | | | | 0.021 | | | |
| *Tissierella praeacuta* | | | | 0.021 | | | 0.042 | 0.023 | | 0.030 | 0.021 | | |
| *Tissierella* sp | 4.448 | 0.381 | 1.782 | 2.218 | 1.677 | 1.001 | 1.277 | 0.867 | 0.398 | 1.697 | 0.555 | 1.003 | 0.220 |
| *Verrucomicrobium* sp | | | | | | | | | | | | | 0.016 |

TABLE 2

Predominant bacterial genera and species in populations H1, C1, P1, S1
and A1. The results are expressed as percentage of total population.

| Species | A1 | C1 | H1 | P1 | S1 | S1-37 | S1-50 | S1-55 | CBP | CB | MF | PB | FE |
|---|---|---|---|---|---|---|---|---|---|---|---|---|---|
| *Bacillus* spp. | 0.994 | 0.635 | 1.969 | 1.368 | 0.483 | | 0.763 | 1.300 | 0.105 | 2.485 | | 0.175 | 0.047 |
| *Caloramator* spp. | 5.045 | 2.669 | 4.295 | 4.063 | 5.200 | 5.765 | 3.608 | 3.351 | 0.126 | 3.378 | 1.623 | 3.176 | 1.369 |
| *Clostridium* spp. | 9.145 | 20.04 | 9.565 | 33.96 | 15.49 | 13.95 | 10.87 | 3.175 | 7.848 | 10.49 | 6.410 | 13.58 | 3.728 |
| *Garciella* sp. | 0.075 | 0.085 | 0.038 | 0.083 | 0.028 | 0.069 | 0.056 | 0.012 | | 0.060 | 0.021 | 0.058 | |

TABLE 2-continued

Predominant bacterial genera and species in populations H1, C1, P1, S1 and A1. The results are expressed as percentage of total population.

| Species | A1 | C1 | H1 | P1 | S1 | S1-37 | S1-50 | S1-55 | CBP | CB | MF | PB | FE |
|---|---|---|---|---|---|---|---|---|---|---|---|---|---|
| *Mahella australiensis* | 0.547 | 0.360 | 0.338 | 0.352 | 0.426 | 0.483 | 0.500 | 0.340 |  | 0.402 | 0.115 | 0.273 | 0.173 |
| *Sporanaerobacter acetigenes* | 77.44 | 74.26 | 80.66 | 53.67 | 75.87 | 78.63 | 81.96 | 85.45 | 90.62 | 81.08 | 90.80 | 81.17 | 92.25 |
| *Tepidanaerobacter* sp. | 2.261 | 1.419 | 1.219 | 4.167 | 0.682 |  | 0.791 | 5.319 | 0.837 | 0.253 | 0.429 | 0.438 |  |
| *Tissierella* spp. | 4.448 | 0.402 | 1.782 | 2.239 | 1.677 | 1.001 | 1.318 | 0.890 | 0.419 | 1.726 | 0.576 | 1.003 | 0.220 |
| Other | 0.050 | 0.127 | 0.131 | 0.104 | 0.142 | 0.104 | 0.139 | 0.164 | 0.042 | 0.119 | 0.021 | 0.127 | 2.218 |
| Sum | 100.0 | 100.0 | 100.0 | 100.0 | 100.0 | 100.0 | 100.0 | 100.0 | 100.0 | 100.0 | 100.0 | 100.0 | 100.0 |

TABLE 3

Correlation coefficients between bacterial diversities of mixed populations calculated from data presented in TABLE 1 using equation [1].

|  | A1 | C1 | H1 | P1 | S1 | S1-37 | S1-50 | S1-55 | CBP | CB | MF | PB | FE |
|---|---|---|---|---|---|---|---|---|---|---|---|---|---|
| A1 | 1 | 0.9970 | 0.9988 | 0.9606 | 0.9982 | 0.9962 | 0.9975 | 0.9951 | 0.9963 | 0.9983 | 0.9977 | 0.9961 | 0.9968 |
| C1 | 0.9970 | 1 | 0.9973 | 0.9722 | 0.9964 | 0.9923 | 0.9953 | 0.9895 | 0.9933 | 0.9944 | 0.9954 | 0.9943 | 0.9940 |
| H1 | 0.9988 | 0.9973 | 1 | 0.9567 | 0.9993 | 0.9981 | 0.9980 | 0.9946 | 0.9975 | 0.9997 | 0.9982 | 0.9972 | 0.9969 |
| P1 | 0.9606 | 0.9722 | 0.9567 | 1 | 0.9607 | 0.9605 | 0.9478 | 0.9428 | 0.9513 | 0.9520 | 0.9533 | 0.9448 | 0.9525 |
| S1 | 0.9982 | 0.9964 | 0.9993 | 0.9607 | 1 | 0.9985 | 0.9955 | 0.9898 | 0.9942 | 0.9976 | 0.9956 | 0.9944 | 0.9936 |
| 37 | 0.9962 | 0.9923 | 0.9981 | 0.9605 | 0.9985 | 1 | 0.9910 | 0.9898 | 0.9917 | 0.9970 | 0.9933 | 0.9887 | 0.9910 |
| 50 | 0.9975 | 0.9953 | 0.9980 | 0.9478 | 0.9955 | 0.9910 | 1 | 0.9959 | 0.9982 | 0.9974 | 0.9984 | 0.9994 | 0.9981 |
| 55 | 0.9951 | 0.9895 | 0.9946 | 0.9428 | 0.9898 | 0.9898 | 0.9959 | 1 | 0.9964 | 0.9948 | 0.9973 | 0.9935 | 0.9995 |
| CBP | 0.9963 | 0.9933 | 0.9975 | 0.9513 | 0.9942 | 0.9917 | 0.9982 | 0.9964 | 1 | 0.9982 | 0.9991 | 0.9974 | 0.9988 |
| CB | 0.9983 | 0.9944 | 0.9997 | 0.9520 | 0.9976 | 0.9970 | 0.9974 | 0.9948 | 0.9982 | 1 | 0.9988 | 0.9959 | 0.9977 |
| MF | 0.9977 | 0.9954 | 0.9982 | 0.9533 | 0.9956 | 0.9933 | 0.9984 | 0.9973 | 0.9991 | 0.9988 | 1 | 0.9967 | 0.9997 |
| PB | 0.9961 | 0.9943 | 0.9972 | 0.9448 | 0.9944 | 0.9887 | 0.9994 | 0.9935 | 0.9974 | 0.9959 | 0.9967 | 1 | 0.9961 |
| FE | 0.9968 | 0.9940 | 0.9969 | 0.9525 | 0.9936 | 0.9910 | 0.9981 | 0.9995 | 0.9988 | 0.9977 | 0.9997 | 0.9961 | 1 |

EXAMPLES

The following examples represent processes and compounds of the present invention.

While the present invention has been described with specificity in accordance with certain embodiments of the present invention, the following examples further serve only to exemplify and illustrate the present invention and are not intended to limit or restrict the effective scope of the present invention.

Example 1

Optimal Conditions for Ammonification by Mixed Populations

To determine the optimal temperature range for ammonification by mixed populations, A1, C1, H1, P1 and S1 were cultured in sterile MBM medium [180 g meat-and-bone meal (MBM) per liter of water] at 50° C. (degrees of Celsius) without aeration for 3 days (d). These cultures, which had reached stationary growth phase, were used as 5% (v/v) (volume per volume) inocula in MBM medium in a total volume of 60 mL (milliliter). Inoculated cultures were incubated at various temperatures without aeration for 7 d (days).

Growth of the mixed bacterial populations was monitored by measuring the ammonium production of the populations. A maximal ammonia level of about 8-10 g/l was repeatedly determined for culture growth under the conditions described above. Therefore, when the ammonia concentration reached this level, it was interpreted as transition to stationary phase of growth. The diverse nature of the populations restricted the use of culture based methods for cell counting, and opacity of the MBM medium prevented the use of optical density measurement for estimation of cell densities. In all the following examples, "inocula of mixed bacterial populations" refer to bacterial cultures, which have reached stationary growth phase.

The extent of ammonification was determined by measuring the ammonia concentration in the inoculated MBM by Ammonium Test 1.10024.0001 (Merck KGaA, Darmstadt, Germany) according to manufacturer's instructions. The result was confirmed with the Ammonia Assay Kit AA0100 (Sigma-Aldrich, Saint Louis, Mo., USA) according to manufacturer's instructions.

Nitrogen content of MBM was determined with the Kjeldahl method by an accredited testing laboratory (Novalab Oy, Karkkila, Finland). Based on this, a maximum ammonia level i.e. the concentration where all proteinacious nitrogen is converted to ammonia was calculated. Nitrogen conversion percentage, i.e. the extent of ammonification of proteinacious nitrogen, was then calculated on the basis of ammonia concentration in the samples. The results are presented in FIG. 1.

The optimal temperature range for ammonification by A1, C1, H1 and P1 is 37-55° C. and by S1 37-60° C. However, S1 was more temperature tolerant than A1, C1, H1 and P1 as S1 retained some of its ammonification efficiency even at room temperature (RT, 23° C.) and 70° C.

Figure 2:
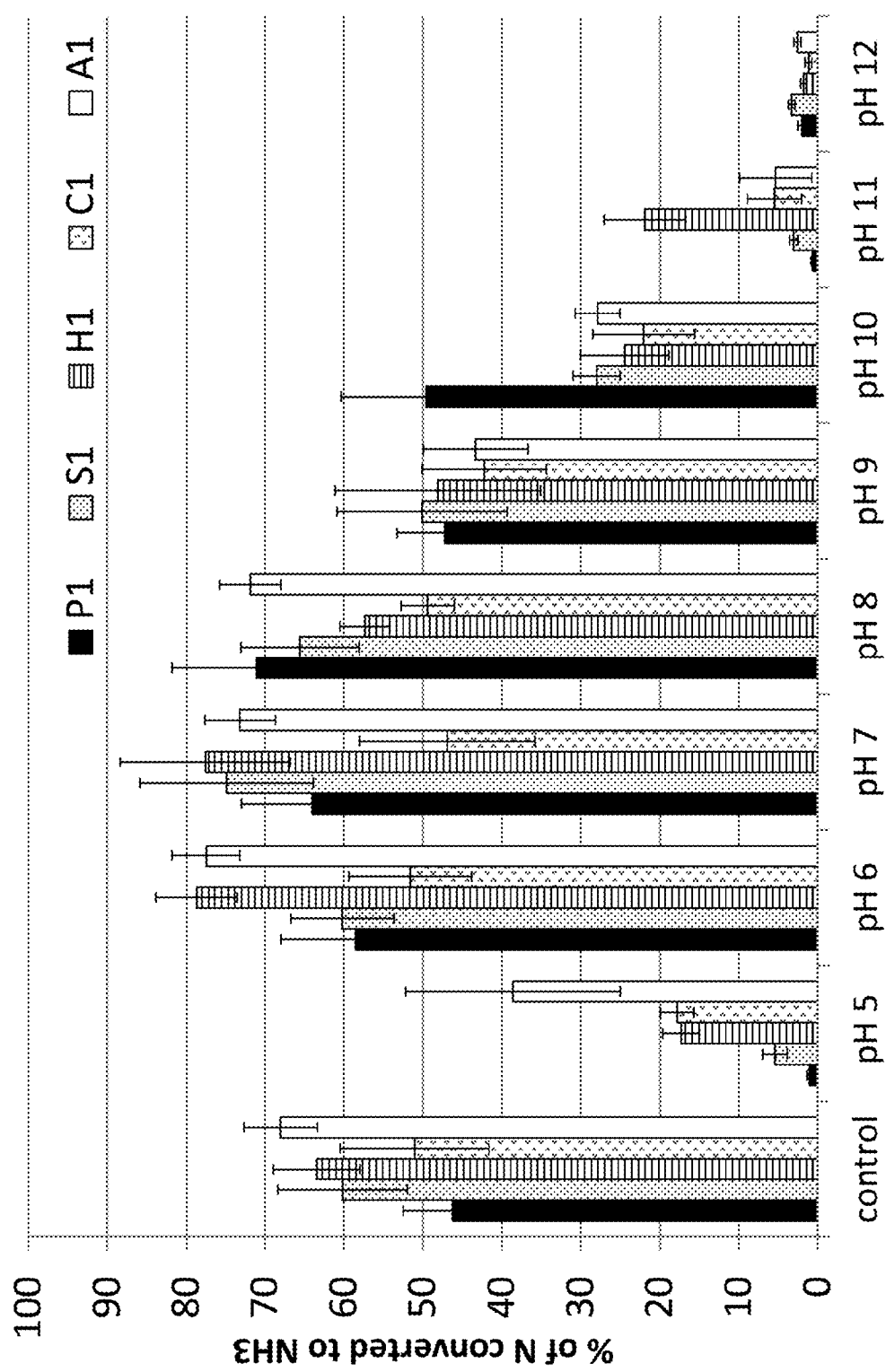
FIG. 2 illustrates the determination of the optimum pH range for ammonification of MBM proteinacious nitrogen by mixed bacterial populations A1, C1, H1, P1, and S1 in Example 1. The results are presented as the percentage of nitrogen converted to ammonia, i.e. ammonification efficiency after 7 days of incubation at 50° C. Error bars indicate standard deviation between two biological replicates. The optimal pH range for ammonification by A1, C1, H1, P1, and S1 is 6-9. "N" indicates nitrogen in compounds to be converted to $NH_3$.
Figure 3C:
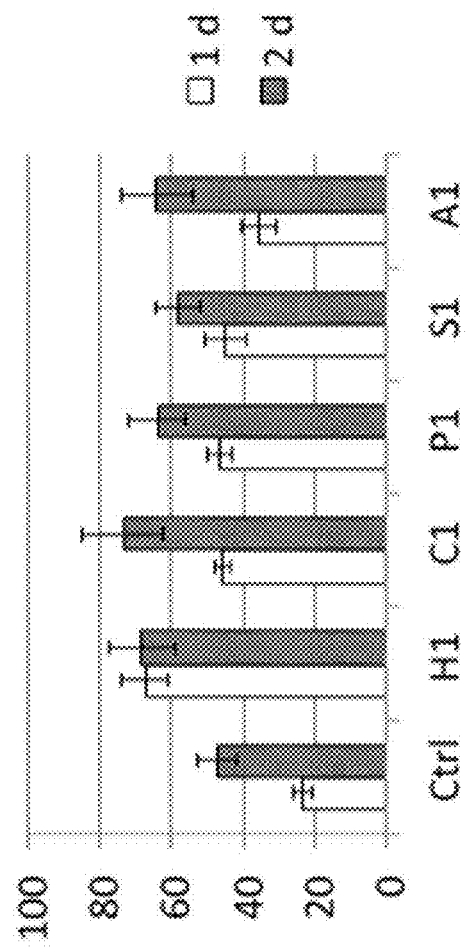
Figure 3D:
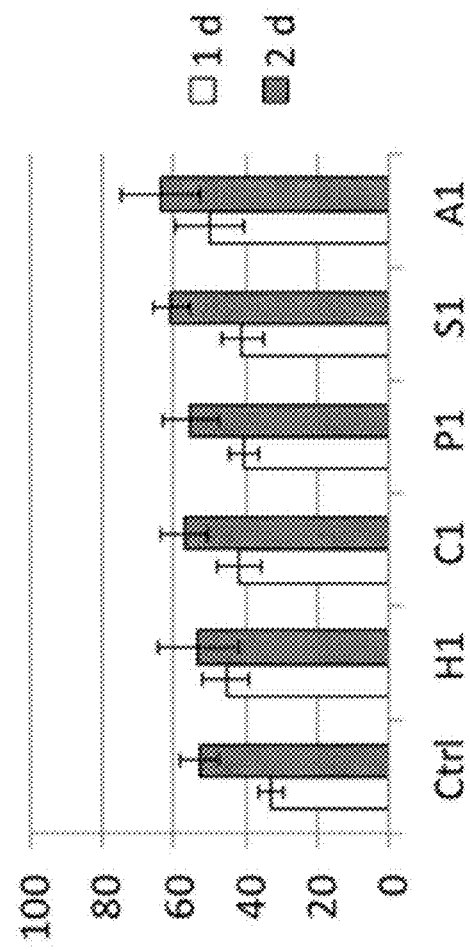
Figure 3E:
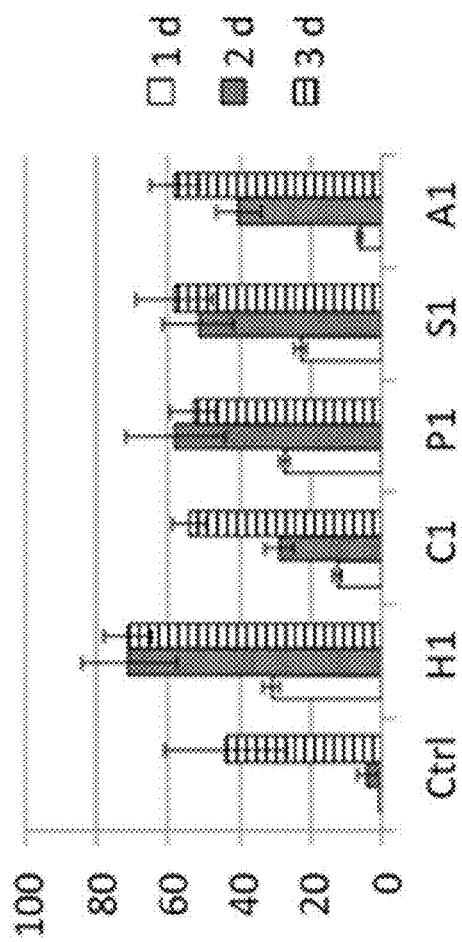
Figure 3F:
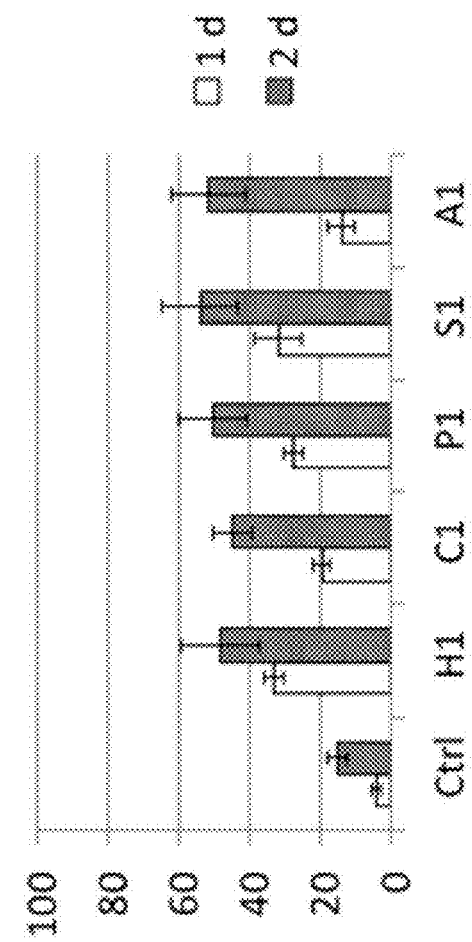
Figure 3G:
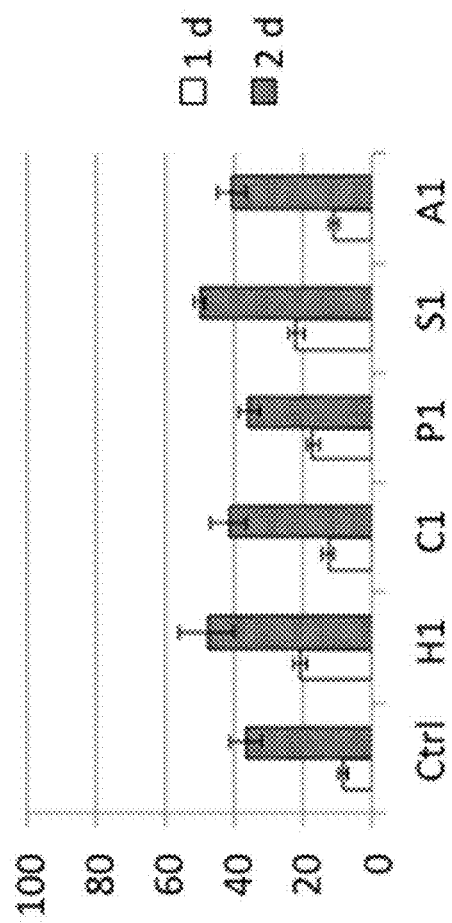
Figure 3H:
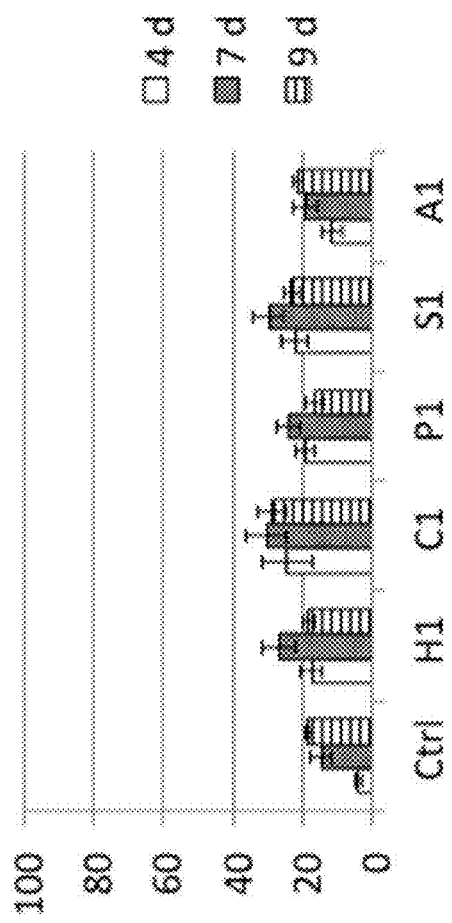

To determine the optimal pH range for ammonification by mixed populations, A1, C1, H1, P1, and S1 were cultured in sterile MBM medium [180 g MBM per liter of water] at 50° C. without aeration for 3 d. These cultures were used as 5% (v/v) inocula in MBM medium in a total volume of 60 mL. The pH of these cultures was then adjusted daily to values ranging from pH 5 to 12. Cultures were incubated at 50° C. for 7 d without aeration. The percentage of nitrogen converted to ammonia was then determined as described hereinabove. The results are presented in FIG. 2.

The optimal pH range for ammonification by A1, C1, H1, P1, and S1 is about pH 6 to about pH 9. All of C1, P1 and S1 show a decrease in ammonification efficiency at pH values below and above the pH 6-9 optimum. It should be noted that population H1 is, however, more tolerant of high pH than the other populations, showing some activity at pH 11, whereas A1 tolerates low pH, also showing activity at pH 5.

To determine optimal oxygen conditions for ammonification by mixed populations, S1 was cultured in sterile MBM medium [180 g MBM per liter of water] at 50° C. without aeration for 3 d. These cultures were used as 5% (v/v) inocula in MBM medium in a total volume of 60 mL. The cultures were incubated anaerobically (in an anaerobic jar with AnaeroGen, Oxoid), microaerobically (in bottles with closed cap), or aerobically (in Erlenmeyer flasks with shaking at speed 90 rpm) at +50° C. for 7 days. Two replicate experiments of each condition were done. Ammonium production of the cultures was measured after 3 and 7 days cultivation using enzymatic determination kit for ammonia (Ammonia Assay Kit AA0100; Sigma-Aldrich), and the percentage of nitrogen converted to ammonia was then determined as described hereinabove.

Ammonia production of the S1 population was not dependent on oxygen level of the cultures. Ammonia yields were 52.5-55.9% in all of the oxygen conditions, after 7 days cultivation (TABLE 4). In conclusion, ammonium production of the S1 population was not dependent on the oxygen level of the medium.

TABLE 4

Percentages of nitrogen converted to ammonium by S1 population cultivated at different oxygen conditions. The results represent averages of two biological replicate experiments. Standard deviations of three replicate measurements from the two biological replicates are shown.

| | % of N converted to ammonia | |
| --- | --- | --- |
| | 3 days | 7 days |
| Anaerobic | 47.6 ± 4.8% | 53.6 ± 4.3% |
| Microaerobic | 40.9 ± 3.7% | 52.5 ± 3.2% |
| Aerobic | 46.4 ± 8.8% | 55.9 ± 5.4% |

Conclusions.

The working range for ammonification of proteinacious materials with mixed bacteria populations was determined. Temperatures from 30° C. to 60° C., more particularly from 37-55° C. and pH 5-11, more particularly from pH 6-9, were the best for bacterial ammonification with the populations described here. Ammonification works in anaerobic, microaerobic, and aerobic conditions using the mixed populations.

Example 2

Enhanced Ammonification of Organic Materials

Mixed bacterial populations H1, C1, P1, S1, and A1 were employed in ammonification of proteinacious nitrogen in various organic, i.e. animal- and plant-origin materials, as defined hereinbelow.

Animal-Origin MBM.

The MBMs (designated infra as MBM1 and MBM2, respectively, were produced from animal by-products according to methods described in EU Commission Regulation 142/2011, and consisted of category 3 (EC Regulation 1069/2009) low infection risk material. In particular, MBM1 was obtained from Findest Protein Oy, Finland, and MBM2 was obtained from SARIA Bio-Industries AG & Co. KG, Germany. Feather meal was obtained from Findest Protein Oy, Finland, and Fish meal was a Polish product obtained from Henry Teirs Ltd, Finland.

Fresh Animal-Origin Materials.

Fresh slaughter by-products of broiler chicken and bovine/porcine origin were used. The broiler by-product consisted of intestines, gizzard, liver, heart, heads, blood, toes, bones, cervical vertebrae, skin of the neck, and visceral fat. The Bovine/porcine by-product consisted of porcine skin, muscle, cartilage, cartilaginous bone, small intestine, heart, lung, kidney, liver, and suet; and bovine muscle, cartilaginous bone, trachea, lung, suet, and green tripe. Fish by-product consisted of fish waste including bone, muscle, skin and viscera. Ground feather was washed feather ground to ≤2 cm particle size. Bovine blood was food grade frozen blood. All fish, poultry, porcine and bovine materials were of Finnish origin.

Plant-Derived Materials.

Bioethanol mask (St1 Oy, Finland) was fermentation waste originating from bioethanol production, Barley briquette (Senson Oy, Finland) was a by-product of wort production, and Barley mask (Senson Oy, Finland) was a by-product of barley enzyme production. Wheat briquette (CropEnergies AG, Germany) and Rape cake (Mildola Oy, Finland) were animal feed materials.

Fresh animal-origin materials were applied as 40% (weight/volume) homogenates and animal-origin meals and plant-derived materials in the concentration of 180 g per liter. Homogenates and solutions were prepared in tap water in a total volume of 60 mL. The pH of homogenates and solutions was adjusted with NaOH to pH 7 if the initial pH was below 7. In addition, plant-origin materials Barley mask, Rape cake, Wheat briquette, and Barley briquette required daily adjustment of pH to 7 after inoculation since pH in these materials dropped to a value below the optimum range for ammonification by mixed populations. Bioethanol mask and all animal-origin materials did not require pH adjustment after inoculation.

Bacterial populations H1, C1, P1, S1, and A1 were cultured in sterile medium [180 g MBM per liter of water] at 50° C. without aeration for 3 d. These cultures were used as 5% (v/v) inocula in homogenates and solutions of organic materials. Inoculated materials and non-inoculated controls were incubated at 50° C. without aeration.

The extent of ammonification was determined by measuring the ammonia concentration in the inoculated organic materials by Ammonium Test 1.10024.0001 (Merck KGaA, Darmstadt, Germany) according to manufacturer's instructions. The result was confirmed with the Ammonia Assay Kit AA0100 (Sigma-Aldrich, Saint Louis, Mo., USA) according to manufacturer's instructions.

Nitrogen content of the organic materials was determined with the Kjeldahl method by an accredited testing laboratory (Novalab Oy, Karkkila, Finland). Based on this, a maximum ammonia level i.e. the concentration where all proteinacious nitrogen is converted to ammonia was calculated for each organic material. Nitrogen conversion percentage, i.e. the extent of ammonification of proteinacious nitrogen, was then calculated on the basis of ammonia concentration in the samples. The results are presented in TABLE 5.

Conclusions.

The results show enhanced ammonification by mixed bacterial populations H1, C1, P1, S1, and A1 as compared to non-inoculated controls. Endogenous bacterial populations are responsible for some extent of ammonification particularly in fresh animal-origin materials, but the process is accelerated by the mixed populations. Plant-based materials show very little endogenous ammonification activity in the conditions used, and benefit significantly from inoculated populations.

Populations H1 and S1 seemed to be the most efficient populations in ammonification. S1 population was the best ammonium producer on fish by-products, fish meal, and MBM2. H1 population was the best ammonium producer on porcine/bovine by-product, MBM1, and bioethanol mask. S1 and H1 populations were not the weakest ammonium producers on any material.

FIGS. 3A-3H illustrate the ammonification efficiency of different organic materials by mixed populations H1, C1, P1, S1, and A1. The organic materials are FIG. 3A: Fish by-product, FIG. 3B: Broiler by-product, FIG. 3C: Bovine/porcine by-product, FIG. 3D: Bioethanol mask, FIG. 3E: Meat-and-bone meal 1, FIG. 3F: Meat-and-bone meal 2, FIG. 3G: Fish meal, FIG. 3H: Feather meal. The results are presented as the percentage of nitrogen converted to ammonia, i.e. ammonification efficiency after incubation at 50° C. for various periods of time. Population S1 stands out as it efficiently ammonified the materials of FIGS. 3A, 3D and 3G, respectively, whereas H1 rapidly ammonifies materials of FIGS. 3A, 3C, 3D and 3E, respectively. All in all, all five populations increase the ammonification efficiency compared to non-inoculated controls. This effect is especially evident in materials 3C, 3D, 3E, and 3F. FIGS. 3A, 3B, 3C, 3D, 3E, 3F, 3G and 3H show results for the materials of FIGS. 3A, 3B, 3C, 3D, 3E, 3F, 3G and 3H, respectively.

cultures were incubated at +50° C. for 2 days. Two replicate experiments with each media were done. Ammonium production was measured after 2 days cultivation using enzymatic determination kit for ammonia (Ammonia Assay Kit AA0100; Sigma-Aldrich).

Results.

Ammonia production by the S1 population was negatively affected by addition of sugars in the medium (Table 6). Without carbohydrate additions, ammonia yield was 60% after 2 days cultivation. Addition of glucose in medium reduced ammonia yields to 34-48%. 1% starch did not reduce ammonia yields, but 5% and 10% starch additions reduced ammonia yields to 45% and 37%, respectively. The lower ammonia yields were associated with lowered pH in the media. In conclusion, ammonium production of S1 population is negatively affected by addition of sugar in the growth medium.

TABLE 6

The effect of sugar or starch additions on ammonia production of S1 population on 40% chicken by-product medium was tested. Ammonium production was measured after 2 days cultivation at +50° C. The results are averages of two biological replicate experiments. Standard deviations of three replicate measurements from both the two biological replicates are shown.

|  | ammonia yield | pH |
|---|---|---|
| 1% glucose | 48.2 ± 7.8% | 7.0 |
| 5% glucose | 34.9 ± 7.9% | 5.8 |
| 10% glucose | 34.3 ± 5.4% | 6 |
| 1% starch | 61.6 ± 7.3% | 7.3 |
| 5% starch | 45.2 ± 7.0% | 6.3 |

TABLE 5

The efficiency of nitrogen conversion to ammonia reported as percentage of maximum. Determination was performed 24 hours from inoculation for the fish, broiler, and porcine/bovine by-products and fish meal, 48 hours from inoculation for meat-and-bone meals, and 168 hours (7 days) from inoculation for feather meal, ground feather, blood and all plant-derived materials. Controls of plant-derived materials were not pH-adjusted.

| | Material/Population | Ctrl | H1 | C1 | P1 | S1 | A1 |
|---|---|---|---|---|---|---|---|
| Fresh animal materials | Fish by-product | 14.9 ± 2.1 | 44.2 ± 8.0 | 31.5 ± 5.4 | 37.1 ± 6.0 | 55.9 ± 7.6 | 28.8 ± 2.6 |
| | Broiler by-product | 32.7 ± 3.3 | 45.4 ± 6.6 | 41.6 ± 6.1 | 40.4 ± 4.3 | 40.8 ± 5.9 | 49.8 ± 9.7 |
| | Porcine/bovine by-product | 23.1 ± 2.8 | 67.2 ± 6.6 | 45.6 ± 2.2 | 46.4 ± 3.6 | 44.9 ± 5.8 | 35.6 ± 5.0 |
| | Ground feather | 43.6 ± 3.4 | n.d. | n.d. | n.d. | 50.1 ± 5.4 | n.d. |
| | Bovine blood | <0.5 | 13.1 ± 3.0 | 34.6 ± 4.3 | 23.1 ± 4.4 | 35.2 ± 5.3 | 11.9 ± 4.3 |
| Animal meals | Feather meal | 14.4 ± 3.1 | 26.8 ± 4.9 | 30.4 ± 5.9 | 23.9 ± 3.7 | 29.7 ± 4.2 | 19.1 ± 3.5 |
| | Fish meal | 8.2 ± 1.1 | 20.7 ± 1.8 | 12.5 ± 1.8 | 16.9 ± 1.9 | 21.9 ± 2.3 | 10.9 ± 1.4 |
| | MBM1 | 3.9 ± 3.4 | 73.2 ± 13.8 | 29.9 ± 4.3 | 60.0 ± 14.6 | 53.4 ± 10.6 | 41.5 ± 6.5 |
| | MBM2 | 15.5 ± 3.0 | 48.9 ± 11.0 | 45.4 ± 5.7 | 50.7 ± 9.8 | 54.7 ± 10.9 | 52.2 ± 10.8 |
| Plant materials | Bioethanol mask | 10.9 ± 2.3 | 103.7 ± 14.1 | 84.3 ± 18.2 | 83.5 ± 10.0 | 102.5 ± 16.7 | 80.4 ± 10.8 |
| | Barley mask | 2.1 ± 1.7 | n.d. | n.d. | n.d. | 61.0 ± 8.4 | n.d. |
| | Rape cake | 2.5 ± 0.6 | 45.7 ± 6.7 | 64.1 ± 10.2 | n.d. | 51.8 ± 6.5 | 58.3 ± 13.6 |
| | Wheat briquette | 3.9 ± 1.5 | 43.9 ± 8.7 | 48.5 ± 8.6 | n.d. | 39.1 ± 10.1 | 40.1 ± 6.4 |
| | Barley briquette | 21.6 ± 3.1 | n.d. | n.d. | n.d. | 61.6 ± 10.1 | n.d. | n.d. = not determined.

Example 3

Ammonification of Mixed Organic Materials (Effect of Carbohydrate Content on Ammonification)

Sugar.

The effect of glucose or starch addition on ammonia production of S1 population was tested on a 40% (weight/volume) chicken by-product medium. Glucose or starch was added in the medium in 1%, 5% and 10% concentrations. S1 population (cultivated on 180 g/l MBM medium) was added as 5% (v/v) inoculum in 60 ml of different media, and the

TABLE 6-continued

The effect of sugar or starch additions on ammonia production of S1 population on 40% chicken by-product medium was tested. Ammonium production was measured after 2 days cultivation at +50° C. The results are averages of two biological replicate experiments. Standard deviations of three replicate measurements from both the two biological replicates are shown.

|  | ammonia yield | pH |
|---|---|---|
| 10% starch | 36.6 ± 5.1% | 5.5 |
| No sugar | 59.7 ± 11.1% | 7.3 |

Mixed Organic Materials.

S1 population was used to ammonify mixtures of materials of plant and animal origin. Culture media with 5 percent dry weight were prepared. Media contained following materials, one material at a time or two materials in 50%+50% proportion: minced chicken by-products (200 g/l alone, 100 g/l in 50-50 mixtures), minced fish by-products (200 g/l alone, 100 g/l in 50-50 mixtures), dried *Chlorella* algae powder (50 g/l alone, 25 g/l in 50-50 mixtures), and barley briquette (50 g/l alone, 25 g/l in 50-50 mixtures). Barley briquettes were mixed also in other proportions with chicken and fish by-products, so that the total dry weight content of the media were always 5%. The materials contained nitrogen as follows: chicken 22.2 g/kg, fish 30.4 g/kg, *Chlorella* 113.6 g/kg, and barley 24.6 g/kg. 7.5 ml of S1 population cultivated in MBM medium (180 g/l) was inoculated in 150 ml of each media. Two replicate experiments of each media were done. The cultures were incubated at +50° C. and ammonium production of the cultures was measured after 4 or 7 days cultivation using a quantitative, enzymatic determination kit for ammonia (Ammonia Assay Kit AA0100; Sigma-Aldrich) for biological samples, according to manufacturer's instructions.

Results (I).

Ammonium was produced in all the materials and their mixtures tested. Nitrogen was converted to ammonia in highest levels (the ammonia yields were highest) in media containing animal materials, that is chicken and fish (72-78%). In media containing plant materials, that is, *Chlorella* and barley, the yields were lower (Table 7). When all the 4 materials were mixed in a medium in 25%+25%+25%+25% proportions, ammonia yield was 67.5±6.7% in 4 days.

TABLE 7

Ammonia production of S1 population in media containing different materials and their mixtures in 4 days. The results are averages of two biological replicate experiments. Standard deviations of three replicate measurements from the two biological replicates are shown.

|  | Chicken | Fish | Chlorella | Barley briquet |
|---|---|---|---|---|
| Chicken | 78.1 ± 16.6% | | | |
| Fish | 71.9 ± 7.9% | 80.2 ± 4.5% | | |
| *Chlorella* | 59.2 ± 9.3% | 59.6 ± 5.4% | 36.0 ± 9.7% | |
| Barley briquet | 37.3 ± 11.1% | 66.2 ± 17.1% | 25.7 ± 7.6% | 23.8 ± 5.4% (7 days cultivation) |

The yields in media containing barley were increased by addition of base to the media during cultivation. When the pH of the cultures was kept at 7-8 by addition of NaOH to the cultures (in the beginning and after 1, 4, 5, and 6 days cultivation), the ammonia yields after 4 days cultivation were as follows: 54.5±9.0% in media containing chicken and barley, 35.6±4.4% in media containing *Chlorella* and barley, and 61.2±7.1% in barley medium (after 7 days cultivation). Referring to the results of negative effect of carbohydrate addition on ammonification, the acidifying effect of barley could be a result of its higher carbohydrate content compared to animal materials.

Results (II).

Barley briquettes were also mixed with chicken by-products and fish by-products in different proportions to determine whether the acidifying effect of barley could be avoided by addition of animal materials in medium in sufficient amounts. These experiments were done in 60 ml volumes.

TABLE 8 shows that in media containing chicken by-products, the maximum proportion of barley in this medium was 30% and after that, the pH dropped under 5 and the ammonia yields were 21% at maximum. In media containing fish by-products, the ammonia yields decreased significantly, when there was less than 40% fish in the medium, and the pH also dropped under pH 5.

TABLE 8

Ammonia production of S1 population in media containing different materials and their mixtures in 3 days. The results are averages of two biological replicate experiments. Standard deviations of three replicate measurements from the two biological replicates are shown.

|  | Ammonia yield (%) | pH |
|---|---|---|
| 100% chicken | 60.3 ± 10.9 | 6.5 |
| 90% chicken + 10% barley | 69.0 ± 6.8 | 6.4 |
| 80% chicken + 20% barley | 35.3 ± 13.2 | 6.1 |
| 70% chicken + 30% barley | 49.3 ± 4.1 | 5.7 |
| 60% chicken + 40% barley | 20.8 ± 2.3 | 4.5 |
| 50% chicken + 50% barley | 20.7 ± 2.1 | 4.3 |
| 100% fish | 79.1 ± 4.4 | 6.7 |
| 80% fish + 20% barley | 85.0 ± 12.5 | 6.8 |
| 60% fish + 40% barley | 81.9 ± 11.0 | 6.4 |
| 50% fish + 50% barley | 87.2 ± 10.4 | 6.1 |
| 40% fish + 60% barley | 73.1 ± 5.4 | 5.8 |
| 30% fish + 80% barley | 33.0 ± 6.5 | 4.9 |
| 20% fish + 80% barley | 36.9 ± 6.2 | 4.4 |

Ammonification of Food Waste with Animal Materials.

Mixtures of minced fish waste and minced food waste were also ammonified by the S1 population. Media containing 40 g raw materials in 100 ml volume were prepared from fish waste with nitrogen content of 27.1 g/kg and food waste with nitrogen content of 10.1 g/kg. The food waste contained both plant and animal materials. Media were adjusted to neutral pH 7. S1 population cultivated in MBM medium (180 g/l) was added as 5% (v/v) inoculum in 60 ml of each media. The cultures were incubated at +50° C. and ammonium production of the cultures was measured after 3 days cultivation using enzymatic determination kit for ammonia (Ammonia Assay Kit AA0100; Sigma-Aldrich).

Results.

The S1 population converted 55-72% of the nitrogen in the media to ammonium in the media containing at least 60% fish waste and at maximum 40% of food waste (Table 9). If there was 50% or less fish waste in the medium, the pH of the cultures dropped to pH 5 or lower, and the ammonia yields decreased to 8-16%. In Example 3 it was also shown that the addition of carbohydrates in the medium caused acidification of the medium and it also had negative effect on ammonification. The high carbohydrate content of food waste is probably the reason for the observed acidification of the media, if its portion in the medium is too high, that is, more than 40%.

TABLE 9

Ammonia production and pH of S1 population cultivated in media containing different proportions of fish and food wastes in 3 days. Standard deviations of three replicate measurements are shown.

| Medium | Ammonia yield (%) | pH |
| --- | --- | --- |
| 100% fish | 61.0 ± 5.8 | 7.5 |
| 90% fish-10% food | 59.9 ± 3.2 | 7.5 |
| 80% fish-20% food | 55.5 ± 2.2 | 7.3 |
| 70% fish-30% food | 57.8 ± 5.0 | 7.3 |
| 60% fish-40% food | 72.2 ± 2.7 | 7.0 |
| 50% fish-50% food | 16.1 ± 0.6 | 5.0 |
| 40% fish-60% food | 13.6 ± 0.8 | 5.0 |
| 30% fish-70% food | 7.7 ± 0.3 | 4.5 |
| 20% fish-80% food | 8.3 ± 0.8 | 4.5 |
| 10% fish-90% food | 7.7 ± 1.2 | 4.5 |
| 100% food | 8.8 ± 1.2 | 4.5 |

Conclusions.

Mixtures of various materials were ammonified using the S1 population. Generally, plant materials were ammonified less efficiently than animal materials. While not wishing to be bound by any hypothesis or theory of the invention, it is possible that this observation is explained by acidification of the medium during cultivation. Acidification of media can be avoided with addition of base in the culture. Also if plant and animal materials were mixed in appropriate proportions, acidification was avoided and higher ammonia yields were achieved.

Example 4

Ammonification in Pilot Scale

The power of the S1 bacterial population in the ammonification of fresh animal materials was shown in 20-25 liters scale. Closed 30 liter vessels made of steel, each containing a temperature controlling system and a stirring mechanism, were used for these fermentation or culture processes. The growth media were 20% suspensions made from broiler by-products or fish by-products. In part of the experiments, 2.5% or 5% (v/v) inoculum of S1 population, cultivated in 180 MBM medium, was added in the culture. The cultures were incubated with moderate constant stirring at +37° C. or at +50° C. for 2-3 days. Ammonia production was measured daily using enzymatic determination kit for ammonia (Ammonia Assay Kit AA0100; Sigma-Aldrich).

Results.

Figure 4:
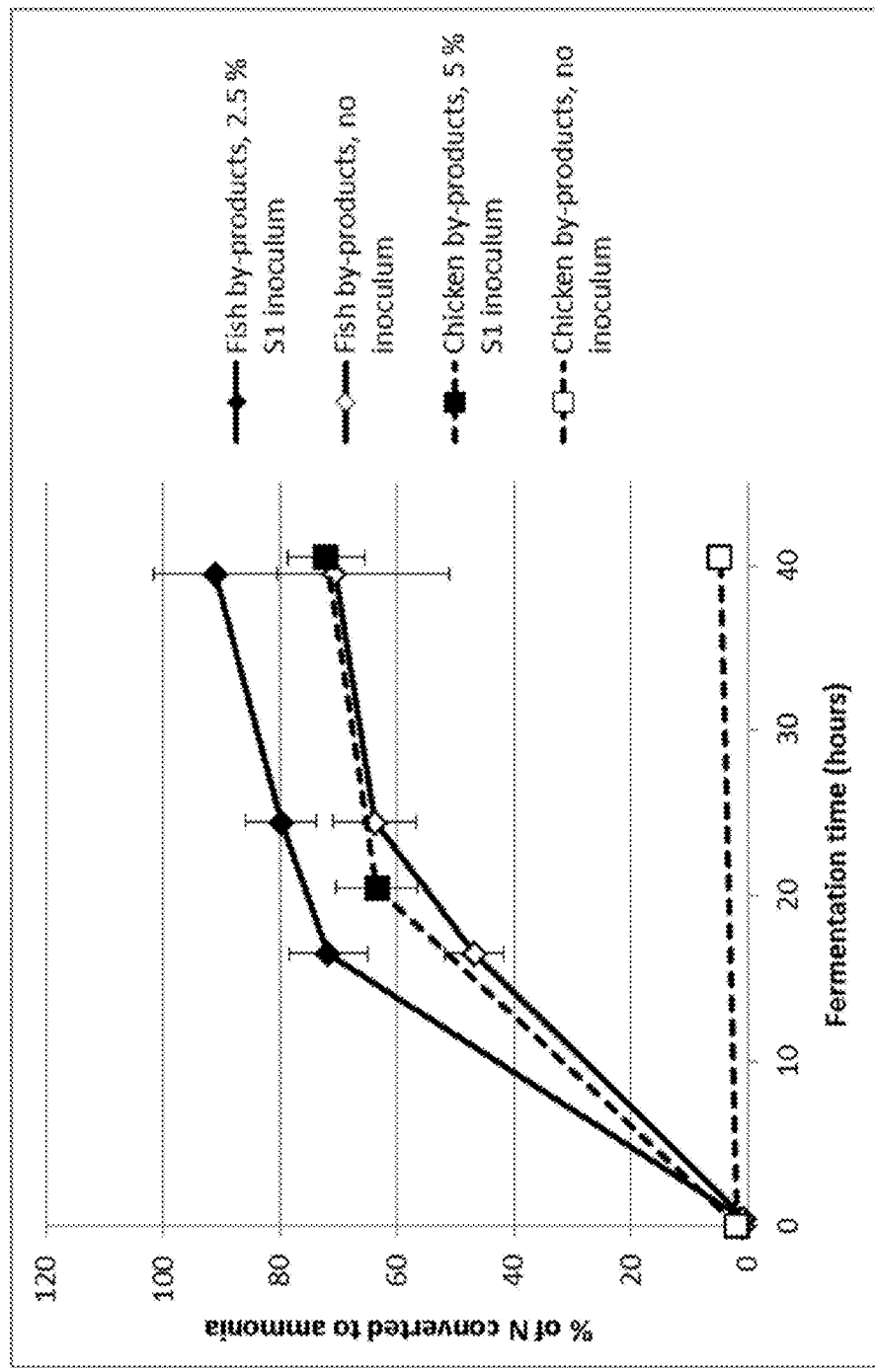
FIG. 4 illustrates ammonification of fish by-product medium and chicken by-product medium in bioreactor at +50° C. without a bacterial inoculum and using the P1 bacterial population in Example 4. The error bars show the standard deviations of three replicate ammonia measurements.

When chicken by-products were incubated at +50° C., in 20 liters volume, the addition of 5% S1 inoculum in the culture was shown to increase ammonia yields significantly (FIG. 4), from 5% to 72% in 40.5 hours. With fish by-products, in 25 liters volume, the addition of 2.5% S1 inoculum increased ammonia yields from 71% to 91% in 39.5 hours, when the cultures were incubated at +50° C.

In fish by-product fermentation or culture processes with the S1 population, cultivation temperatures +37° C. and +50° C. were compared. After 24 hours of culture, the ammonia yields were higher, 80±6%, at +50° C. and lower, 58±6% at +37° C. This confirmed that +50° C. is a good temperature for ammonification of proteinacious materials with the S1 bacteria population.

Conclusions.

These results, achieved at 20-25 liters scale, confirmed the results of Example 2, which showed that the addition of a bacteria population increased the ammonia yields in media containing animal derived materials.

Example 5

Induction of Mixed Populations from Meat-and-Bone Meal

A1 population was created as follows: *Aspergillus oryzae* CECT 2095 was cultivated on potato dextrose agar (ATCC medium 336, recipe is as follows: Boil 300 grams of finely diced potatoes in 500 ml of water until thoroughly cooked. Filter and add water to filtrate to 1000 ml. Add 20 g glucose and 15 g agar, and autoclave at 121° C.) for about 7 days. Three milliliters of potato dextrose liquid medium (prepared as potato dextrose agar but without addition of agar) was poured on the *A. oryzae* agar culture, and the suspension was transferred in 100 ml of potato dextrose medium. The culture was incubated at room temperature with gentle shaking for 3 days. Then, a solid state medium of MBM1 was prepared by mixing 36 g non-sterile MBM1 with 50 ml of tap water. 10 ml of *A. oryzae* liquid culture was inoculated on the solid state medium, and the culture was incubated at +30° C. for 16 days. Then, water was added in the culture to get concentration of 180 g MBM per liter of water. This liquid culture was incubated at +50° C. for 4 days.

C1 population was created by mixing non-sterile MBM1 with cold tap water in a proportion of 180 g MBM per liter of water. MBM was cultured without aeration at 50° C. until $NH_3$ concentration leveled out, and stationary growth phase was reached as explained in EXAMPLE 1.

H1 population was created by mixing non-sterile MBM1 with boiling tap water in a proportion of 180 g MBM per liter of water. The mixture was let cool to room temperature. MBM was cultured without aeration at 50° C. until $NH_3$ concentration leveled out, and stationary growth phase was reached as explained in EXAMPLE 1.

P1 population was created by mixing non-sterile MBM1 with cold tap water in a proportion of 45 g MBM per liter of water. The mixture was buffered to pH 9 with 20 mM MOPS, and cultured without aeration at 50° C. The culture that had reached stationary growth phase was then used to inoculate sterile MBM1 medium, and cultured without aeration at 50° C. until stationary phase. Inoculation and culturing were repeated seven times. Therefore, P1 represents the $8^{th}$ generation of original MBM1 population.

S1 population was created by mixing non-sterile MBM2 with cold tap water in a proportion of 180 g MBM per liter of water. MBM was cultured without aeration at 50° C. until $NH_3$ concentration leveled out, and stationary growth phase was reached as explained in EXAMPLE 1.

All populations were maintained by storing the liquid culture at +4° C. This culture was used to inoculate the cultures used in EXAMPLES 1 to 6.

Effect of Temperature.

To determine the optimal temperature for enrichment of ammonifying bacteria populations from non-sterile MBM, non-sterile MBM media (180 g MBM1 or MBM2 per liter of cold tap water) were prepared and buffered to pH 7.5-8 with 20 mM MOPS. The media were incubated at various temperatures between room temperature (RT) and 80° C. for 7 days without aeration. $NH_3$ concentrations were determined as explained in EXAMPLE 1. Results are presented in FIG. 5.

Results.

Figure 5:
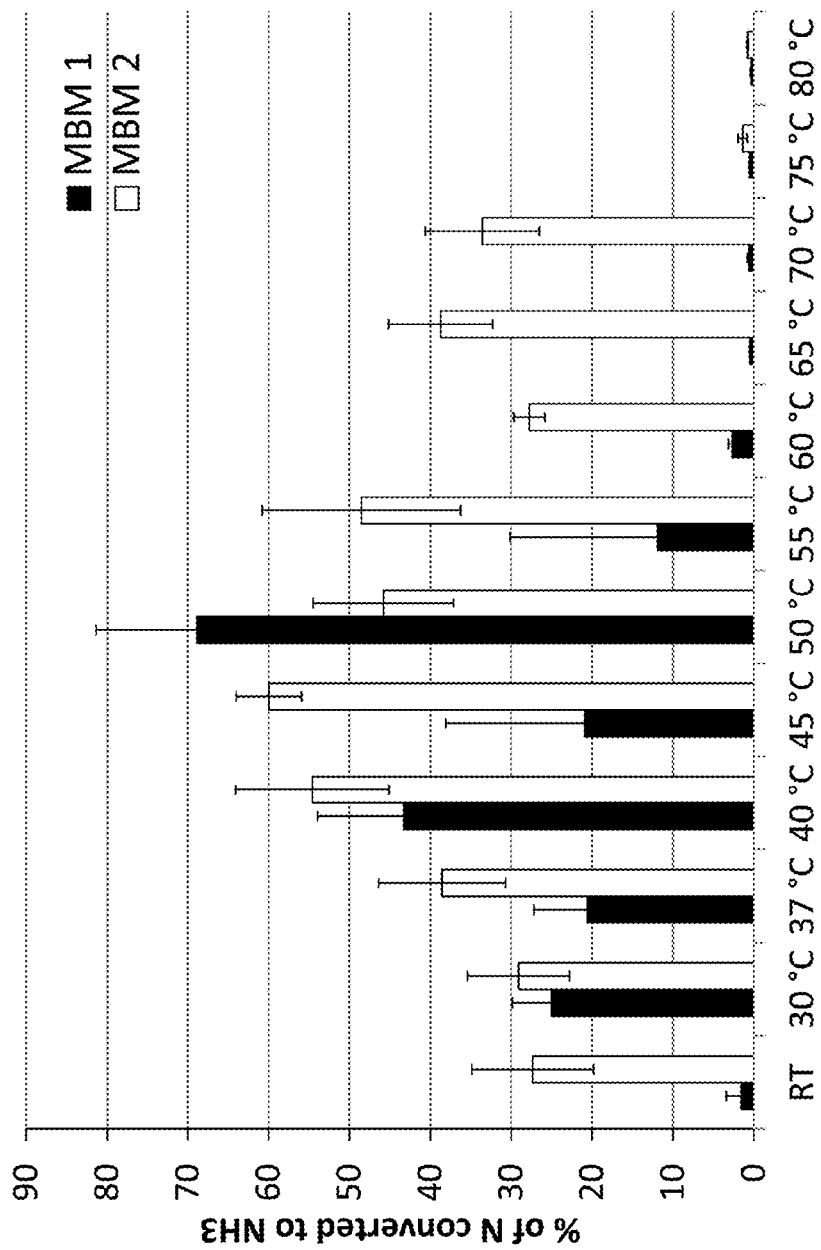
FIG. 5 illustrates determination of the temperature range for inducing mixed populations from non-sterile meat-and-bone meal ("MBM") from two different manufacturers (MBM1 and MBM2) in Example 5. The results are presented as the percentage of nitrogen converted to ammonia, i.e. ammonification efficiency after 7 days of incubation at various temperatures. Error bars indicate standard deviation between two biological replicates except MBM1 at 45° C. and 55° C. with 4 and 7 replicates, respectively. MBM2 populations are induced efficiently between room temperature (RT) and 70° C., whereas MBM1 has an optimum for efficient nitrogen conversion at 50° C. "RT" indicates room temperature.

The optimum temperature for inducing a population on MBM1 is 50° C. (FIG. 5). The slightly lower temperature, 45° C., seems to lie between a mesophilic and thermophilic population as seen from the high deviation between results at this temperature. In some of the biological replicate samples there was high nitrogen conversion efficiency, whereas some showed low recoveries. The thermophilic population has a sharp optimum, as at 55° C. the population is not induced in all biological replicate samples. MBM2 had a high potential for population induction at a wide range of temperatures, RT-70° C. MBM2 population is active in ammonification at a wider range of temperatures than MBM1 population Effect of pH.

To determine the optimal pH for enrichment of ammonifying bacteria populations from non-sterile MBM, non-sterile MBM media (180 g MBM per liter of water) were prepared and their pH was adjusted at different levels (pH 5, 6, 7, 8, 9, 10, 11, or 12) or left unadjusted. These media were incubated at +50° C. for 7 days without aeration. During the cultivation, in one experiment the pH's were adjusted on the original level at days 1, 2, 3, and 4. In another experiment, pH was not adjusted during cultivation. Meat-and-bone meals from two different manufacturers (MBM1 and MBM2) were tested.

Results.

The optimal pH range for enrichment of ammonifying populations from MBM1 was 7-9, if pH of the cultures was adjusted daily (TABLE 10). If pH was adjusted only in the beginning of the cultivation, optimal pH range was 8-11. In MBM2, optimal pH range was 6-9, if pH was adjusted daily. If pH was adjusted only in the beginning of the experiment, pH's from 5 to 11 were all equally good for enrichment of ammonifying bacteria.

TABLE 10

Effect of the pH of the culture on enrichment of ammonifying bacteria populations from non-sterile MBM1 and MBM2. Culture pH was adjusted either in the beginning of the experiment or daily. Standard deviations of two biological replicate experiments and three technical replicate measurements of each sample are shown.

| | MBM1 | | MBM2 | |
| --- | --- | --- | --- | --- |
| | pH adjusted in the beginning | pH adjusted daily | pH adjusted in the beginning | pH adjusted daily |
| pH 5 | 13.1 ± 1.1 | 1.1 ± 0.7 | 38.3 ± 2.6 | 5.6 ± 0.5 |
| pH 6 | 26.6 ± 9.8 | 25.8 ± 5.9 | 38.0 ± 5.6 | 36.6 ± 3.5 |
| pH 7 | 37.1 ± 11.5 | 42.9 ± 4.1 | 37.6 ± 2.0 | 47.9 ± 3.9 |
| pH 8 | 67.4 ± 7.7 | 55.5 ± 4.6 | 44.4 ± 5.8 | 56.2 ± 5.1 |
| pH 9 | 71.3 ± 1.8 | 41.2 ± 4.0 | 39.7 ± 5.8 | 51.2 ± 1.7 |
| pH 10 | 60.0 ± 7.4 | 11.1 ± 0.5 | 41.3 ± 5.9 | 9.0 ± 1.2 |
| pH 11 | 51.7 ± 4.7 | 0.9 ± 0.1 | 45.6 ± 2.9 | 1.5 ± 0.2 |
| pH 12 | 1.0 ± 0.2 | 1.3 ± 0.2 | 17.0 ± 1.0 | 1.5 ± 0.2 |
| no pH adjustment | 43.8 ± 12.9 | | 42.0 ± 8.4 | |

Conclusions.

Mixed populations can be induced from meat-and-bone meals from two different manufacturers. Populations are induced at various temperatures, but optima vary between MBMs. If pH is maintained at below 6 or above 9, population induction is inhibited from both MBMs.

Example 6

Pre-Treatment of Plant-Derived Materials for Ammonification with *Aspergillus Oryzae*

Ammonification of carbohydrate-rich plant materials with mixed bacteria populations may cause acidification of the culture as described in Examples 2 and 3. In this experiment, plant materials were pre-treated with *Aspergillus oryzae* to decrease the acidifying effect of plant materials in ammonification.

Rape cake, wheat briquettes, barley briquettes, barley mash, and food waste (containing mainly plant materials but also some meat) were first hydrolyzed with *Aspergillus oryzae* CECT 2095. Media containing 36 g rape cake or wheat briquettes and 90 ml tap water were prepared in Erlenmeyer flasks of 1 liter volume. Media containing 18 g barley briquettes and 45 ml tap water, 18 g barley mash and 20 ml tap water, or 32 g food waste and 43 ml tap water were prepared in Erlenmeyer flasks of 500 ml volume. Rape cake and wheat briquette media were either autoclaved at +121° C. to sterilize the media or left non-sterile. Barley media and food waste medium were left non-sterile.

*A. oryzae* CECT 2095 was first cultivated on potato dextrose agar plate (300 g diced potatoes were boiled in 500 ml of water until thoroughly cooked, the liquid was filtered and water was added to 1000 ml; 20 g glucose and 15 g agar was added; the medium was autoclaved at +121° C. and poured on agar plates) for 3-7 days at room temperature. Then, *A. oryzae* was inoculated in potato dextrose liquid medium (prepared as potato dextrose agar but without agar) and cultivated at room temperature with gentle shaking for 3-5 days. 10 ml and 5 ml of the liquid culture was inoculated on the media in 1 liter and 500 ml Erlenmeyer flasks, respectively. The final concentration of the media were as follows: rape cake, wheat briquettes, and barley briquettes 360 g/l, barley mash 720 g/l, and food waste 400 g/l.

All the cultures were incubated at +30° C. for 14 days. Then, the cultures were weighed and water was added in the cultures as much as water was evaporated from the cultures during cultivation. The media hydrolyzed with *A. oryzae* were ammonified using mixed bacteria population S1. First, tap water was added on the cultures to get media with concentrations of 90 g plant material per liter of water. Food waste media were kept in the original 40% concentration. A 5% (v/v) S1 incouclum was added in 40 or 60 ml of the media, and the cultures were incubated at +50° C. for 7 days, and the ammonium production in the cultures was determined using an enzymatic determination kit for ammonia (Ammonia Assay Kit AA0100; Sigma-Aldrich).

As a control, rape cake, wheat briquettes, barley briquettes, barley mash, and food waste were ammonified with S1 population without any pretreatments. Media containing 180 g/l wheat briquettes, rape cake, barley briquettes, or barley mash per liter of water and a 40% suspension of food waste was prepared in tap water. A 5% inoculum of S1 population was added in 40 or 60 ml of the media, and the cultures were incubated at +50° C. for 7 days. pH's of the cultures were either left unadjusted or then pH was adjusted daily (at days 0, 1, 2, 3, and 4) to neutral level using NaOH. Ammonium production of the cultures was determined using an enzymatic determination kit for ammonia (Ammonia Assay Kit AA0100; Sigma-Aldrich).

Results.

After 14 days pre-treatment with *A. oryzae*, pH of the cultures was 7-9. In all the non-pretreated plant media, the pH was acidic. Pre-treatment of plant-derived materials with *A. oryzae* increased ammonia yields 1.7-8-fold when compared to the non-pre-treated plant materials (TABLE 11). A similar increase in ammonium production was obtained with daily adjustment of the culture pH with NaOH. Thus, the pre-treatment of plant materials with *A. oryzae* is an alternative means to overcome the acidifying effect of carbohydrate-rich plant materials in ammonification. Plant materials can be either sterilized before the *A. oryzae* pre-treatment, or left non-sterile.

TABLE 11

Ammonium production of S1 population on different plant materials
with or without daily pH adjustment (non-sterile media were used) or
with 14 days pre-treatment with *A. oryzae* (the media were either
non-sterile or sterilized before inoculation of *A. oryzae*). Ammonium
production is represented as percentage of N converted to nitrogen
in 7 days. The results are averages of two biological replicate
experiments and three replicate measurements of each sample.
In the experiment with *A. oryzae*, two biological replicate *A. oryzae*
cultivations and two biological replicate S1 cultivations were made.

|  | no pH adjustment | pH adjusted | pre-treatment with *A. oryzae* (non-sterile) | pre-treatment with *A. oryzae* (sterile) |
|---|---|---|---|---|
| Barley briquet | 28.2 ± 3.1% | 68.3 ± 10.1% | 47.5 ± 9.8% |  |
| Barley mash | 14.5 ± 1.6% | 72.9 ± 8.4% | 73.1 ± 11.4% |  |
| Rape cake | 7.2 ± 1.5% | 42.4 ± 10.1% | 58.2 ± 4.4% | 52.8 ± 7.1% |
| Wheat | 5.5 ± 0.6% | 55.0 ± 6.6% | 21.7 ± 4.2% | 32.4 ± 2.8% |
| Food | 8.6 ± 0.7% | 44.9 ± 9.7% | 67.4 ± 8.0% |  |

Example 7

Innate Populations and Inoculated Meat-and-Bone Meal-Derived Populations as Ammonifying Communities Bacterial community analysis of innate populations of broiler chicken by-product (CBP-M), porcine/bovine by-product (PB-M), chicken feather (FE-M), fish by-product (MF-M) and crushed porcine/bovine bone (CB-M) was performed on DNA obtained by phenol-chloroform-isoamyl alcohol extraction from cultures where cells had been disrupted by bead beating. Cultured populations were raised and harvested from 20% (weight/volume) materials incubated at 50° C. for four days (FE for 8 days). Bacterial 16S gene assay by tag-encoded FLX amplicon pyrosequencing (bTEFAP) and bacterial diversity data analysis were performed by the Research and Testing Lab (Lubbock, Tex., USA) as described by Dowd et al. 2008a and Wolcott et al. 2009. Primers 28F 'GAGTTTGATCNTGGCTCAG' (SEQ ID NO: 1) and 519R 'GTNTTACNGCGGCKGCTG' (SEQ ID NO: 2) were used for amplification of 16S variable regions V1-3.

Results.

Bacterial diversity analysis of innate and inoculated communities revealed the presence of bacteria belonging to 58 different genera (TABLE 12). Of the total of 115 results, 79 were identified at the species level and 36 at the genus level. TABLE 13 presents the predominant bacterial genera and species in each population. Bacteria belonging to 5-9 different genera form the majority of the populations. *Clostridium* spp. and *Sporanaerobacter acetigenes* are predominant in populations derived from materials inoculated with S1 as well as innate populations of PB-M and MF-M. The other three innate populations showed more variety: CBP-M consisted predominantly of *Enterococcus* spp. and *Pediococcus* spp., FE-M population of *Petrobacter succinatimandens*, *Soehngenia saccharolpica*, *Tissierella* sp., and *Clostridium* spp., and CB-M population of *Leptothrix* sp. and *Schlegelella* spp.

Correlation coefficients (TABLE 14) were calculated from data presented in TABLE 12 using equation [1], where X and Y refer to two matrices, e.g. CBP-M and CBP, between which the correlation is calculated, x and y are single values within a matrix, and $\bar{x}$ and $\bar{y}$ are the means of all values within a matrix. Species not present in the population (empty cells in TABLE 12) were assigned a value 0.

$$\mathrm{Correl}(X, Y) = \frac{\Sigma(x - \bar{x})(y - \bar{y})}{\sqrt{\Sigma(x - \bar{x})^2 \Sigma(y - \bar{y})^2}} \qquad [1]$$

TABLE 14 reveals a high similarity between populations in all five inoculated materials and innate populations PB-M and MF-M. The remaining innate populations CBP-M, FE-M, and CB-M show low similarity mutually as well as to other populations. As stated above based on results of TABLE 3, S1 outcompetes innate populations present in animal-origin materials. However, a population similar to S1 can arise in animal-origin materials (PB-M and MF-M) under the conditions used. This is likely, since meat-and-bone meal, the source of S1 and other efficiently ammonifying populations A1, C1, H1, and P1 (see EXAMPLE 5), is manufactured from slaughter by-products of various animal species. However, comparison of innate and inoculated populations of CBP, FE, and CB shows the bacterial community can evolve to a different composition under similar conditions. TABLE 14 also indicates ammonium yield i.e. the percentage of nitrogen in the animal-origin material converted to ammonia at the moment of harvesting the population for DNA extraction. The yields correlate with similarity of the innate population to inoculated population. Yields of 40% or above are reached only when the correlation coefficient is above 0.9, and preferably above 0.95.

TABLE 12

Bacterial diversity analysis results: genera and species in populations
innate to animal-origin materials: broiler chicken by-product (CBP-M),
porcine/bovine by-product (PB-M), chicken feather (FE-M), fish by-product (MF-M)
and crushed porcine/bovine bone (CB-M). Diversity analysis was also performed on
the same materials inoculated with 5% (volume/volume) meat-and-bone meal-
derived population S1. These results are labeled CBP, PB, FE, MF or CB, and are the
same presented in TABLE 1. The results are expressed as percentage of total population.

| Species | CBP-M | CBP | PB-M | PB | FE-M | FE | MF-M | MF | CB-M | CB |
|---|---|---|---|---|---|---|---|---|---|---|
| *Acidovorax temperans* |  |  |  |  | 0.06 |  |  |  |  |  |
| *Aneurinibacillus thermoaerophilus* |  |  | 0.08 |  |  |  |  |  |  |  |
| *Bacillus coagulans* | 0.64 |  |  |  |  |  |  |  |  |  |
| *Bacillus licheniformis* |  |  |  |  |  |  |  |  | 1.55 |  |
| *Bacillus* sp. | 1.56 | 0.10 |  | 0.13 | 0.11 | 0.03 | 0.01 |  | 0.08 | 2.20 |
| *Bacillus thermoamylovorans* |  |  | 0.06 | 0.05 |  | 0.02 | 0.16 |  |  | 0.28 |
| *Brevibacillus agri* |  |  |  |  | 0.22 |  |  |  |  |  |

TABLE 12-continued

Bacterial diversity analysis results: genera and species in populations innate to animal-origin materials: broiler chicken by-product (CBP-M), porcine/bovine by-product (PB-M), chicken feather (FE-M), fish by-product (MF-M) and crushed porcine/bovine bone (CB-M). Diversity analysis was also performed on the same materials inoculated with 5% (volume/volume) meat-and-bone meal-derived population S1. These results are labeled CBP, PB, FE, MF or CB, and are the same presented in TABLE 1. The results are expressed as percentage of total population.

| Species | CBP-M | CBP | PB-M | PB | FE-M | FE | MF-M | MF | CB-M | CB |
|---|---|---|---|---|---|---|---|---|---|---|
| *Burkholderia endofungorum* | | | | | | | | | 0.01 | |
| *Burkholderia* sp. | | | | | | | | | 0.01 | |
| *Butyrivibrio fibrisolvens* | | | 0.02 | | | | | | | |
| *Caldicoprobacter oshimai* | | | | | | | | 0.02 | | 0.03 |
| *Caloramator* sp. | | 0.13 | | 3.18 | 0.56 | 1.37 | | 1.62 | 0.06 | 3.38 |
| *Carnobacterium divergens* | 0.20 | 0.02 | 0.03 | | | | | | | 0.01 |
| *Carnobacterium* sp. | 0.09 | | 0.03 | | | | | | | |
| *Catabacter* sp. | | | | 0.02 | | | | | | 0.03 |
| *Cerasibacillus quisquiliarum* | | | 0.05 | | | | | | | |
| *Clostridium botulinum* | | 1.13 | | 6.23 | 0.20 | 0.25 | | 1.17 | 0.01 | 1.43 |
| *Clostridium cochlearium* | 0.02 | 2.89 | 15.03 | 2.16 | | 0.96 | 30.47 | 2.93 | 0.01 | 5.98 |
| *Clostridium gasigenes* | | | | | | | | | | 0.01 |
| *Clostridium haemolyticum* | | 0.06 | | | | | | | | |
| *Clostridium methylpentosum* | 0.03 | | | | | | | | | |
| *Clostridium nexile* | 0.02 | | | | | | | | | |
| *Clostridium novyi* | | 0.08 | | | | | | | | |
| *Clostridium oceanicum* | | | | 0.03 | | | | | | |
| *Clostridium pasteurianum* | | | 0.02 | | | | | | | |
| *Clostridium perfringens* | | | 0.01 | 0.14 | | | | | | |
| *Clostridium* sp. | 0.61 | 0.42 | | 0.67 | 0.11 | 0.28 | | 0.17 | 0.01 | 0.51 |
| *Clostridium sporogenes* | | 3.03 | 3.18 | 4.12 | 3.75 | 0.03 | 2.84 | 0.22 | | 1.67 |
| *Clostridium subterminale* | | | | | 0.03 | | | | | |
| *Clostridium tetani* | | | 0.01 | | | | | | | |
| *Clostridium ultunense* | | 0.23 | | 0.22 | 6.64 | 2.20 | 0.01 | 1.92 | 0.03 | 0.89 |
| *Corynebacterium kroppenstedtii* | | | | | | | | | | 0.01 |
| *Corynebacterium pseudogenitalium* | | | | | | 0.02 | | | | 0.01 |
| *Cyanobacterium* sp | | | | | | 0.02 | | | | |
| *Enterococcus avium* | 0.05 | | | | | | | | | |
| *Enterococcus azikeevi* | 0.33 | | | | | | | | | |
| *Enterococcus casseliflavus* | 0.02 | | | | | | | | | |
| *Enterococcus cecorum* | | | 0.01 | | | | | | | |
| *Enterococcus devriesei* | 0.11 | | | | | | | | | |
| *Enterococcus durans* | 0.02 | | | | | | | | | |
| *Enterococcus faecalis* | 4.08 | | | | | 0.08 | | | | |
| *Enterococcus faecium* | 15.49 | | 0.01 | | | | | | 0.24 | |
| *Enterococcus gallinarum* | 0.05 | | | | | | | | | |
| *Enterococcus hermanniensis* | 0.03 | | | | | | | | | |
| *Enterococcus hirae* | 0.78 | | | | | | | | | |
| *Enterococcus raffinosus* | 0.05 | | | | | | | | | |
| *Enterococcus* sp. | 0.26 | | 0.05 | | | 0.06 | | | | |
| *Eubacterium* sp. | 0.11 | | | | | | | | | |
| *Faecalibacterium prausnitzii* | 0.09 | | | | | | | | | |
| *Faecalibacterium* sp. | | | | 0.05 | | | | | | |
| *Garciella* sp. | | | | 0.06 | | | | 0.02 | | 0.06 |
| *Gemella haemolysans* | | | 0.01 | | | | | | | |
| *Geobacter grbiciae* | | | | 0.01 | | | | | | |
| *Granulicatella elegans* | 0.06 | | | | 0.03 | | | | | |
| *Granulicatella* sp. | 0.02 | | | | | | | | | |
| *Lactobacillus curvatus* | 0.22 | | | | | | | | | |
| *Lactobacillus johnsonii* | 0.09 | | | | | 0.05 | | | | |
| *Lactobacillus oligofermentans* | 0.06 | | | | | | | | | |
| *Lactobacillus pontis* | 0.02 | | | | | | | | | |
| *Lactobacillus reuteri* | 0.14 | | | | | | | | | |
| *Lactobacillus sakei* | 0.17 | | | | | | | | | |
| *Lactobacillus* sp | 0.14 | | | | | | | | | |
| *Lactococcus garvieae* | 1.39 | | | | | | | | | |
| *Lactococcus lactis* | 0.17 | | | | | | | | | |
| *Lactococcus piscium* | | | 0.01 | | | | | | 0.02 | |
| *Lactococcus raffinolactis* | 0.23 | | | | | | | | | |

TABLE 12-continued

Bacterial diversity analysis results: genera and species in populations innate to animal-origin materials: broiler chicken by-product (CBP-M), porcine/bovine by-product (PB-M), chicken feather (FE-M), fish by-product (MF-M) and crushed porcine/bovine bone (CB-M). Diversity analysis was also performed on the same materials inoculated with 5% (volume/volume) meat-and-bone meal-derived population S1. These results are labeled CBP, PB, FE, MF or CB, and are the same presented in TABLE 1. The results are expressed as percentage of total population.

| Species | CBP-M | CBP | PB-M | PB | FE-M | FE | MF-M | MF | CB-M | CB |
|---|---|---|---|---|---|---|---|---|---|---|
| *Lactococcus* sp | 2.63 | | 0.06 | | | | | | | |
| *Lautropia* sp. | | | | | | | | | 0.01 | |
| *Leptothrix* sp. | | | | | | | | | 35.27 | |
| *Macrococcus caseolyticus* | | | | | | 1.93 | | | | |
| *Mahella australiensis* | | | | 0.27 | 0.34 | 0.17 | | 0.12 | 0.05 | 0.40 |
| *Mycobacterium phocaicum* | | | | | | 0.02 | | | | |
| *Natronincola ferrireducens* | | | 0.02 | | | | | | | |
| *Niastella* sp. | 0.03 | | | | | | | | | |
| *Octadecabacter* sp. | | | | | | | 0.01 | | | |
| *Pediococcus acidilactici* | 67.58 | | 0.01 | | | | | | | |
| *Pediococcus* sp. | 0.09 | | | | | | | | | |
| *Peptostreptococcus* sp | | | 1.81 | | | | | | | |
| *Petrobacter succinatimandens* | 0.05 | | | | | 37.89 | | | | |
| *Propionibacterium acnes* | | 0.02 | | 0.01 | | | | | | |
| *Pseudobutyrivibrio ruminis* | | | | | | | | | | 0.01 |
| *Pseudoxanthomonas taiwanensis* | | | | | | 0.67 | | | | |
| *Rhodobacter* sp. | | | | 0.02 | | | | | | |
| *Ruminococcus albus* | 0.03 | | | | | | | | | |
| *Ruminococcus* sp. | | | | | | 0.02 | | | | |
| *Salicola marasensis* | | | | | | | | | 0.01 | |
| *Sarcina* sp. | | | | | | 0.02 | | | | |
| *Schlegelella* sp. | | | | | | | | | 0.72 | |
| *Schlegelella thermodepolymerans* | | | | | | | | | 60.58 | |
| *Soehngenia saccharolytica* | | | | | | 30.69 | | | | |
| *Sporanaerobacter acetigenes* | 0.02 | 90.62 | 78.83 | 81.17 | 0.03 | 92.24 | 64.14 | 90.80 | 1.33 | 81.08 |
| *Sporomusa aerivorans* | | | | | 0.03 | | | | | |
| *Sporomusa* sp. | | | | | 0.06 | | | | | |
| *Sporotalea propionica* | | | | | 0.20 | | | | | |
| *Sporotalea* sp. | | | | | 0.03 | | | | | |
| *Streptococcus alactolyticus* | 0.08 | | | | | | | | | |
| *Streptococcus parauberis* | 0.05 | | | | | | | | | |
| *Streptococcus* sp. | 0.12 | | | | | | | | | |
| *Subdoligranulum* sp. | 0.06 | | | 0.01 | | | | | | |
| *Subdoligranulum variabile* | 0.12 | | | | | | | | | |
| *Tateyamaria* sp. | | | | | | | 0.01 | | | |
| *Tepidanaerobacter* sp. | | 0.84 | 0.60 | 0.44 | | | 2.33 | 0.43 | | 0.25 |
| *Thermoanaerobacterium aciditolerans* | 0.02 | | | | | | | | | |
| *Thermoanaerobacterium aotearoense* | 0.93 | | | | | | | | | |
| *Thermoanaerobacterium* sp | 0.02 | | | | | | | | | |
| *Thermoanaerobacterium thermosaccharolyticum* | 0.76 | | | | | | | | | |
| *Thermosediminibacter* sp. | | | | 0.01 | | | | | | |
| *Tissierella creatinophila* | | 0.02 | | | | | | | | |
| *Tissierella praeacuta* | | | | | | | | | 0.02 | 0.03 |
| *Tissierella* sp. | | 0.40 | 0.08 | 1.00 | 18.09 | 0.22 | 0.01 | 0.56 | 0.03 | 1.70 |
| *Trichococcus* sp. | 0.02 | | | | | | | | | |
| *Vagococcus* sp. | 0.05 | | | | | | | | | |
| *Verrucomicrobium* sp. | | | | | | 0.02 | | | | |
| *Weissella* sp. | 0.02 | | | | | | | | | |
| *Xanthomonas campestris* | | | | | | 0.28 | | | | |

TABLE 13

Predominant bacterial genera and species in populations CBP-M, CBP, PB-M, PB, FE-M, FE, MF-M, MF, CB-M, and CB. The results are expressed as percentage of total population.

| Species | CBP-M | CBP | PB-M | PB | FE-M | FE | MF-M | MF | CB-M | CB |
|---|---|---|---|---|---|---|---|---|---|---|
| *Bacillus* spp. | 2.20 | 0.10 | 0.06 | 0.18 | 0.11 | 0.05 | 0.17 | | 1.63 | 2.49 |
| *Caloramator* spp. | | 0.13 | | 3.18 | 0.56 | 1.37 | | 1.62 | 0.06 | 3.38 |
| *Clostridium* spp. | 0.67 | 7.85 | 18.25 | 13.58 | 10.73 | 3.73 | 33.33 | 6.41 | 0.06 | 10.49 |
| *Enterococcus* spp. | 21.25 | | 0.07 | | | 0.14 | | | 0.24 | |
| *Lactobacillus* spp. | 0.84 | | | | | 0.05 | | | | |
| *Lactococcus* spp. | 4.43 | | 0.07 | | | | | | 0.02 | |
| *Leptothrix* sp. | | | | | | | | | 35.27 | |
| *Macrococcus caseolyticus* | | | | | | 1.93 | | | | |
| *Pediococcus* spp. | 67.67 | | 0.01 | | | | | | | |
| *Peptostreptococcus* sp. | | | 1.81 | | | | | | | |
| *Petrobacter succinatimandens* | 0.05 | | | | 37.89 | | | | | |
| *Schlegelella* spp. | | | | | | | | | 61.29 | |
| *Soehngenia saccharolytica* | | | | | 30.69 | | | | | |
| *Sporanaerobacter acetigenes* | 0.02 | 90.62 | 78.83 | 81.17 | 0.03 | 92.24 | 64.14 | 90.80 | 1.33 | 81.08 |
| *Tepidanaerobacter* sp. | | 0.84 | 0.60 | 0.44 | | | 2.33 | 0.43 | | 0.25 |
| *Thermoanaerobacterium* spp. | 1.73 | | | | | | | | | |
| *Tissierella* spp. | | 0.42 | 0.08 | 1.00 | 18.09 | 0.22 | 0.01 | 0.58 | 0.03 | 1.73 |
| OTHER | 1.15 | 0.04 | 0.23 | 0.46 | 1.90 | 0.27 | 0.02 | 0.16 | 0.08 | 0.58 |
| TOTAL | 100 | 100 | 100 | 100 | 100 | 100 | 100 | 100 | 100 | 100 |

TABLE 14

Correlation coefficients between bacterial diversities of mixed populations calculated from data presented in TABLE 12 using equation [1]. Yield (last row) is the percentage of nitrogen in the animal-origin material converted to ammonia at the moment of harvesting the population for DNA extraction.

| | CBP-M | CBP | PB-M | PB | FE-M | FE | MF-M | MF | CB-M | CB |
|---|---|---|---|---|---|---|---|---|---|---|
| CBP_M | 1 | −0.0137 | −0.0154 | −0.0152 | −0.0238 | −0.0134 | −0.0176 | −0.0137 | −0.0173 | −0.0147 |
| CBP | −0.0137 | 1 | 0.9874 | 0.9971 | −0.0137 | 0.9986 | 0.9155 | 0.9992 | 0.0053 | 0.9977 |
| PB_M | −0.0154 | 0.9874 | 1 | 0.9827 | −0.0173 | 0.9824 | 0.9667 | 0.9863 | 0.0032 | 0.9912 |
| PB | −0.0152 | 0.9971 | 0.9827 | 1 | −0.0111 | 0.9951 | 0.9094 | 0.9964 | 0.0038 | 0.9963 |
| FE_M | −0.0238 | −0.0137 | −0.0173 | −0.0111 | 1 | −0.0136 | −0.0204 | −0.0127 | −0.0239 | −0.0094 |
| FE | −0.0134 | 0.9986 | 0.9824 | 0.9951 | −0.0136 | 1 | 0.9050 | 0.9995 | 0.0056 | 0.9965 |
| MF_M | −0.0176 | 0.9155 | 0.9667 | 0.9094 | −0.0204 | 0.9050 | 1 | 0.9144 | −0.0003 | 0.9293 |
| MF | −0.0137 | 0.9992 | 0.9863 | 0.9964 | −0.0127 | 0.9995 | 0.9144 | 1 | 0.0054 | 0.9982 |
| CB_M | −0.0173 | 0.0053 | 0.0032 | 0.0038 | −0.0239 | 0.0056 | −0.0003 | 0.0054 | 1 | 0.0038 |
| CB | −0.0147 | 0.9977 | 0.9912 | 0.9963 | −0.0094 | 0.9965 | 0.9293 | 0.9982 | 0.0038 | 1 |
| yield % | 7.4 | 89.4 | 54.9 | 94.9 | 25.0 | 50.1 | 63.3 | 91.3 | 6.5 | 71.4 |

Example 8

Efficiency of Ammonification by Populations Derived From Soil and Meat-and-Bone Meal To compare bacterial community composition and ammonification performance of populations derived from meat-and-bone meal and other sources, natural populations were cultured from forest and field soils.

FO1 and FI1 populations were created by mixing non-sterile forest (FO) or field (FI) soil with cold tap water in a proportion of 180 g soil per liter of water. The mixture was cultured without aeration at 50° C. FO2 and FI2 populations were created by mixing non-sterile forest (FO) or field (FI) soil with boiling tap water in a proportion of 180 g of soil per liter of water. The mixture was let cool to room temperature. All mixtures were incubated without aeration at 50° C. After 7 days incubation, 5 ml of each culture was inoculated in 100 ml of sterile MBM1 medium containing 180 g of MBM1 per liter of water. The cultures were incubated at 50° C. for 7 days.

Bacterial community analysis of soil populations was performed on DNA obtained by phenol-chloroform-isoamyl alcohol extraction from cultures where cells had been disrupted by bead beating. Bacterial 16S gene assay by tag-encoded FLX amplicon pyrosequencing (bTEFAP) and bacterial diversity data analysis were performed by the Research and Testing Lab (Lubbock, Tex., USA) as described by Dowd et al. 2008a and Wolcott et al. 2009. Primers 28F 'GAGTTTGATCNTGGCTCAG' (SEQ ID NO: 1) and 519R 'GTNTTACNGCGGCKGCTG' (SEQ ID NO: 2) were used for amplification of 16S variable regions V1-3.

Results.

Bacterial diversity analysis of soil- and MBM-derived populations revealed the presence of bacteria belonging to 45 different genera (TABLE 15). Of the total of 85 results, 66 were identified at the species level and 19 at the genus level.

TABLE 16 presents the predominant bacterial genera and species in each population. Bacteria belonging to 6-7 different genera form the majority of the populations. *Clostridium* spp. and *Sporanaerobacter acetigenes* are predominant in MBM-derived populations well as FO1 and FI1. The other two soil populations showed more variety: FO2 consisted predominantly of *Bacillus* spp., *Thermoanaerobacterium* spp., and *Clostridium* spp., and FI2 of *Clostridium* spp., *Tissierella* sp., and *Caloramator* sp.

Correlation coefficients (TABLE 17) were calculated from data presented in TABLE 15 using equation [1], where X and Y refer to two matrices, e.g. A1 and C1, between which the correlation is calculated, x and y are single values within a matrix, and $\bar{x}$ and $\bar{y}$ are the means of all values within a matrix. Species not present in the population (empty cells in TABLE 15) were assigned a value 0.

$$\mathrm{Correl}(X, Y) = \frac{\Sigma(x - \bar{x})(y - \bar{y})}{\sqrt{\Sigma(x - \bar{x})^2 \Sigma(y - \bar{y})^2}} \quad [1]$$

TABLE 17 shows a high similarity (correlation coefficient >0.9) between all five MBM-derived populations, as well as soil populations FO1 and FI1. Therefore, populations similar to MBM-derived populations can arise from soil. Correlation coefficients of FO2 and FI2 are below 0.2, indicating low similarity. Therefore, dissolving soil in boiling water is lethal to bacteria important to ammonification. TABLE 17 also indicates ammonium yield i.e. the percentage of nitrogen in MBM converted to ammonia at the moment of harvesting the population for DNA extraction. The yields correlate with similarity of the innate population to inoculated population. Yields of 40% or above are reached only when the correlation coefficient is above 0.9.

TABLE 15

Bacterial community diversity analysis results: genera and species in soil- and meat-and-bone meal-derived populations A1, C1, H1, P1, and S1. The results of the meat-and-bone meal-derived populations A1, C1, H1, P1, and S1 are the same presented in TABLE 1. The results are expressed as percentage of total population.

| Species | A1 | C1 | H1 | P1 | S1 | FO1 | FO2 | FI1 | FI2 |
|---|---|---|---|---|---|---|---|---|---|
| *Alicyclobacillus contaminans* | | | | | | | 0.23 | | |
| *Aneurinibacillus thermoaerophilus* | | | | | | | | | 0.12 |
| *Bacillus beijingensis* | | | | | | 0.04 | 0.02 | | |
| *Bacillus benzoevorans* | | | | | | | 0.02 | | |
| *Bacillus coagulans* | | | | | | 0.34 | 8.71 | | |
| *Bacillus ginsengi* | | | | | | | 0.02 | | |
| *Bacillus nealsonii* | | | | | | | 0.06 | | |
| *Bacillus pichinotyi* | | | | | | | 0.02 | | |
| *Bacillus smithii* | | | | | | | 0.02 | | |
| *Bacillus* sp. | 0.77 | 0.53 | 1.46 | 0.97 | 0.40 | 1.22 | 29.82 | | 0.18 |
| *Bacillus thermoamylovorans* | 0.22 | 0.11 | 0.51 | 0.39 | 0.09 | | | | |
| *Bacillus vireti* | | | | | | | 0.04 | | |
| *Butyrivibrio fibrisolvens* | | 0.02 | | | | | | | 0.02 |
| *Caldicoprobacter oshimai* | 0.05 | 0.04 | 0.11 | 0.02 | 0.09 | | | | 0.02 |
| *Caloramator fervidus* | | | | 0.02 | | | | | |
| *Caloramator* sp. | 5.04 | 2.67 | 4.29 | 4.04 | 5.20 | 3.61 | | 0.75 | 7.66 |
| *Carnobacterium divergens* | | | | | | | 0.06 | | |
| *Catabacter* sp. | | | | 0.02 | | | | | |
| *Clostridium beijerinckii* | | | | | | | 0.04 | | |
| *Clostridium botulinum* | | 6.95 | | 6.61 | 4.63 | 2.88 | | | |
| *Clostridium cochlearium* | 5.79 | 6.44 | 6.92 | 11.84 | 8.50 | 6.59 | 0.06 | 1.80 | 16.38 |
| *Clostridium haemolyticum* | | 0.06 | | | | | | | |
| *Clostridium hveragerdense* | | | | | | | | | 0.02 |
| *Clostridium limosum* | | | | | | | | | 0.02 |
| *Clostridium oceanicum* | | 0.06 | | 0.02 | 0.06 | 0.08 | | | |
| *Clostridium pasteurianum* | | | | | | | 0.45 | | |
| *Clostridium purinilyticum* | | | | | | | | 0.03 | |
| *Clostridium* sp. | 0.22 | 0.49 | 0.62 | 0.12 | 0.57 | 1.11 | 16.16 | 6.34 | 9.27 |
| *Clostridium sporogenes* | 0.55 | 0.53 | 1.18 | 0.19 | 0.48 | 1.24 | 0.06 | 3.68 | 22.37 |
| *Clostridium thiosulfatireducens* | | | | | | | | | 0.02 |
| *Clostridium tyrobutyricum* | | | | | | | 0.06 | | |
| *Clostridium ultunense* | 2.58 | 5.51 | 0.84 | 15.17 | 1.25 | 0.01 | | 2.82 | 4.01 |
| *Clostridium xylanovorans* | | | | | | | 0.08 | | |
| *Empedobacter brevis* | | | | | | | 0.02 | | |
| *Enterobacter cloacae* | | | | | | | 0.02 | | |
| *Enterococcus azikeevi* | | | | | | | 0.04 | | |
| *Enterococcus faecalis* | | | | | | | 0.30 | | |
| *Enterococcus faecium* | | | | | | | 1.06 | | |
| *Enterococcus hirae* | | | | | | | 0.04 | 0.05 | |
| *Enterococcus raffinosus* | | | | | | | 0.02 | | |
| *Enterococcus* sp. | | | | | | | 0.02 | | |
| *Faecalibacterium prausnitzii* | | | | | | | 0.02 | | 0.02 |
| *Faecalibacterium* sp. | | 0.02 | | | | 0.04 | | 0.03 | 0.04 |
| *Fervidicola ferrireducens* | | | | 0.02 | | | | | |
| *Garciella* sp. | 0.07 | 0.08 | 0.04 | 0.08 | 0.03 | 0.01 | | | 0.04 |
| *Halobacillus trueperi* | | | | | | | 0.04 | | |
| *Klebsiella oxytoca* | | | | | | | 0.04 | | |

TABLE 15-continued

Bacterial community diversity analysis results: genera and species in
soil- and meat-and-bone meal-derived populations A1, C1, H1, P1, and S1. The
results of the meat-and-bone meal-derived populations A1, C1, H1, P1, and S1 are the
same presented in TABLE 1. The results are expressed as percentage of total population.

| Species | A1 | C1 | H1 | P1 | S1 | FO1 | FO2 | FI1 | FI2 |
|---|---|---|---|---|---|---|---|---|---|
| *Lactobacillus crispatus* | | | | 0.04 | | | | | |
| *Lactobacillus pontis* | | | | | | | 0.02 | | |
| *Lactococcus garvieae* | | | | | | | 0.13 | | |
| *Lactococcus raffinolactis* | | | | | | | 0.06 | | |
| *Lactococcus* sp. | | | | | | | 0.13 | | |
| *Leptospira broomii* | | 0.02 | | | | | | | |
| *Mahella australiensis* | 0.55 | 0.36 | 0.34 | 0.35 | 0.43 | 1.34 | | 0.35 | 4.59 |
| *Microbacterium aurum* | | 0.02 | | | | | | | |
| *Pantoea* sp. | | | | | | | 0.02 | | |
| *Pediococcus acidilactici* | | | | | | | 4.80 | | |
| *Pelosinus* sp. | | | | | | | | | 0.02 |
| *Peptostreptococcus* sp. | | | | | | 0.01 | | 0.19 | 0.27 |
| *Petrobacter succinatimandens* | | | | | | | 0.04 | | |
| *Propionibacterium* sp. | | | | 0.03 | | | | | |
| *Pseudobutyrivibrio ruminis* | | | | 0.03 | | | | | |
| *Schlegelella thermodepolymerans* | | | | | | | 0.13 | | |
| *Shigella flexneri* | | | | | | | 0.02 | | |
| *Soehngenia* sp. | | | | | | | | 0.03 | |
| *Sphingomonas mucosissima* | | 0.02 | | | | | | | |
| *Sporanaerobacter acetigenes* | 77.44 | 74.26 | 80.66 | 53.67 | 75.87 | 80.50 | 0.04 | 77.63 | |
| *Sporolactobacillus inulinus* | | | | | | | 0.08 | | |
| *Sporotalea* sp. | | | | | | | | | 0.02 |
| *Streptococcus alactolyticus* | | | | | | | 0.02 | | |
| *Streptococcus mitis* | | | | | | | | 0.03 | |
| *Subdoligranulum variabile* | | | | | | | 0.06 | | |
| *Symbiobacterium* sp. | | | | | | 0.12 | | | |
| *Tepidanaerobacter* sp. | 2.26 | 1.42 | 1.22 | 4.17 | 0.68 | 0.12 | | 1.29 | 4.48 |
| *Tepidimicrobium ferriphilum* | | | | | | | | | 0.51 |
| *Thermoanaerobacterium aciditolerans* | | | | | | 0.50 | 0.89 | | |
| *Thermoanaerobacterium aotearoense* | | | | | | | 19.97 | | |
| *Thermoanaerobacterium islandicum* | | | | | | 0.01 | | | |
| *Thermoanaerobacterium* sp. | | | | | | 0.04 | 0.28 | | |
| *Thermoanaerobacterium thermosaccharolyticum* | | | | | | 0.10 | 15.65 | | |
| *Thermosediminibacter* sp. | | | | | | 0.07 | | | |
| *Tissierella creatinophila* | | 0.02 | | | | | | | |
| *Tissierella praeacuta* | | | | 0.02 | | | | | |
| *Tissierella* sp. | 4.45 | 0.38 | 1.78 | 2.22 | 1.68 | | 0.02 | 4.97 | 29.93 |
| *Tuberibacillus calidus* | | | | | | | 0.02 | | |

TABLE 16

Predominant bacterial genera and species in MBM- and soil-derived
populations. The results are expressed as percentage of total population.

| Species | A1 | C1 | H1 | P1 | S1 | FO1 | FO2 | FI1 | FI2 |
|---|---|---|---|---|---|---|---|---|---|
| *Bacillus* spp. | 0.99 | 0.64 | 1.97 | 1.37 | 0.48 | 1.60 | 38.74 | | 0.18 |
| *Caloramator* spp. | 5.04 | 2.67 | 4.29 | 4.06 | 5.20 | 3.61 | | 0.75 | 7.66 |
| *Clostridium* spp. | 9.15 | 20.04 | 9.56 | 33.96 | 15.49 | 11.91 | 16.93 | 14.68 | 52.08 |
| *Enterococcus* spp. | | | | | | | 1.49 | 0.05 | |
| *Mahella australiensis* | 0.55 | 0.36 | 0.34 | 0.35 | 0.43 | 1.34 | | 0.35 | 4.59 |
| *Pediococcus* spp. | | | | | | | 4.80 | | |
| *Sporanaerobacter acetigenes* | 77.44 | 74.26 | 80.66 | 53.67 | 75.87 | 80.50 | 0.04 | 77.63 | |
| *Tepidanaerobacter* sp. | 2.26 | 1.42 | 1.22 | 4.17 | 0.68 | 0.12 | | 1.29 | 4.48 |
| *Thermoanaerobacterium* spp. | | | | | | | 0.65 | 36.79 | |
| *Tissierella* spp. | 4.45 | 0.40 | 1.78 | 2.24 | 1.68 | | 0.02 | 4.97 | 29.93 |
| OTHER | 0.12 | 0.21 | 0.17 | 0.19 | 0.17 | 0.26 | 1.19 | 0.27 | 1.08 |
| TOTAL | 100 | 100 | 100 | 100 | 100 | 100 | 100 | 100 | 100 |

TABLE 17

Correlation coefficients between bacterial diversities of mixed populations calculated from data presented in TABLE 15 using equation [1]. Yield (last row) is the percentage of nitrogen in the animal-origin material converted to ammonia at the moment of harvesting the population for DNA extraction.

|  | A1 | C1 | H1 | P1 | S1 | FO1 | FO2 | FI1 | FI2 |
|---|---|---|---|---|---|---|---|---|---|
| A1 | 1 | 0.9929 | 0.9988 | 0.9554 | 0.9964 | 0.9963 | −0.0268 | 0.9930 | 0.0577 |
| C1 | 0.9929 | 1 | 0.9933 | 0.9704 | 0.9968 | 0.9952 | −0.0288 | 0.9872 | 0.0213 |
| H1 | 0.9988 | 0.9933 | 1 | 0.9505 | 0.9975 | 0.9988 | −0.0177 | 0.9924 | 0.0371 |
| P1 | 0.9554 | 0.9704 | 0.9505 | 1 | 0.9597 | 0.9490 | −0.0349 | 0.9409 | 0.1097 |
| S1 | 0.9964 | 0.9968 | 0.9975 | 0.9597 | 1 | 0.9984 | −0.0290 | 0.9877 | 0.0434 |
| FO1 | 0.9963 | 0.9952 | 0.9988 | 0.9490 | 0.9984 | 1 | −0.0161 | 0.9911 | 0.0187 |
| FO2 | −0.0268 | −0.0288 | −0.0177 | −0.0349 | −0.0290 | −0.0161 | 1 | −0.0035 | 0.0230 |
| FI1 | 0.9930 | 0.9872 | 0.9924 | 0.9409 | 0.9877 | 0.9911 | −0.0035 | 1 | 0.0699 |
| FI2 | 0.0577 | 0.0213 | 0.0371 | 0.1097 | 0.0434 | 0.0187 | 0.0230 | 0.0699 | 1 |
| yield % | 55.0 | 43.1 | 61.5 | 47.6 | 58.5 | 46.5 | 0.4 | 44.6 | 27.0 |

Example 9

Efficiency of Ammonification by Populations Derived from Cow Rumen and Meat-and-Bone Meal To compare ammonification performance of populations derived from meat-and-bone meal to other sources, bovine rumen population was studied. Excessive ammonia production is a major nutritional inefficiency in ruminants. The majority of amino acid catabolizing and therefore ammonia-producing activity of rumen has been attributed to certain microbes termed hyper ammonia-producing bacteria (HAB) (Russell et al. 1988; Chen and Russell 1989; Krause and Russell 1996, Eschenlauer et al. 2002). Therefore, rumen can be a source of efficiently ammonifying bacteria.

Enrichment of an ammonifying population was attempted by successive rounds of culturing bovine rumen bacteria in sterile MBM1. Bovine rumen content was obtained from a fistulated cow, and filtered to separate liquid from solids. The liquid was added to sterile MBM1 medium [180 g meat-and-bone meal 1 per liter of water] as a 25% (volume/volume) inoculum, and cultured without aeration at 37° C. Each enrichment cycle lasted 7 days to allow the ammonification reaction to reach full extent.

Results.

Ammonia yield i.e. the percentage of nitrogen converted to ammonia increased from 12.3%±6.6% to 24.7%±3.1% during the first three enrichment cycles, but then remained at the same level during the following four cycles. As shown in FIG. 1 in EXAMPLE 1, MBM-derived populations produce higher ammonia yields ranging from 37.9%±2.3% to 58.8%±13.9% at 37° C. Therefore, despite of enrichment, the rumen population remained less efficient in ammonification than MBM-derived populations.

The enriched rumen populations were not subjected to community diversity analysis. Fouts et al. (2012) report in their study of ruminal populations of twelve cows that eighty percent of bacteria identified to species level were belonged to orders *Clostridiales, Bacteroidales, Elysipelotrichales* and unclassified TM7. This composition differs from the composition of MBM-derived populations A1, C1, H1, P1, and S1 (TABLE 2), 94-98% of which consist of bacteria belonging to order *Clostridiales* (genera *Caloramator, Clostridium, Sporanaerobacter, Garciella* and *Tissierella*).

DISCUSSION

Based on the experiments, it is clear that ammonification using defined mixed populations results in superior yields compared to prior art. Using the populations described above, ammonia concentrations up to 12 g/l have been achieved, depending on the protein content of the starting material/medium used. This is 15-30 times improvement on ammonification yields in comparison with the prior art. Typically, 50-80 percent of the total nitrogen in the media was found to be converted to ammonia within 24-48 hours.

Figure 6:
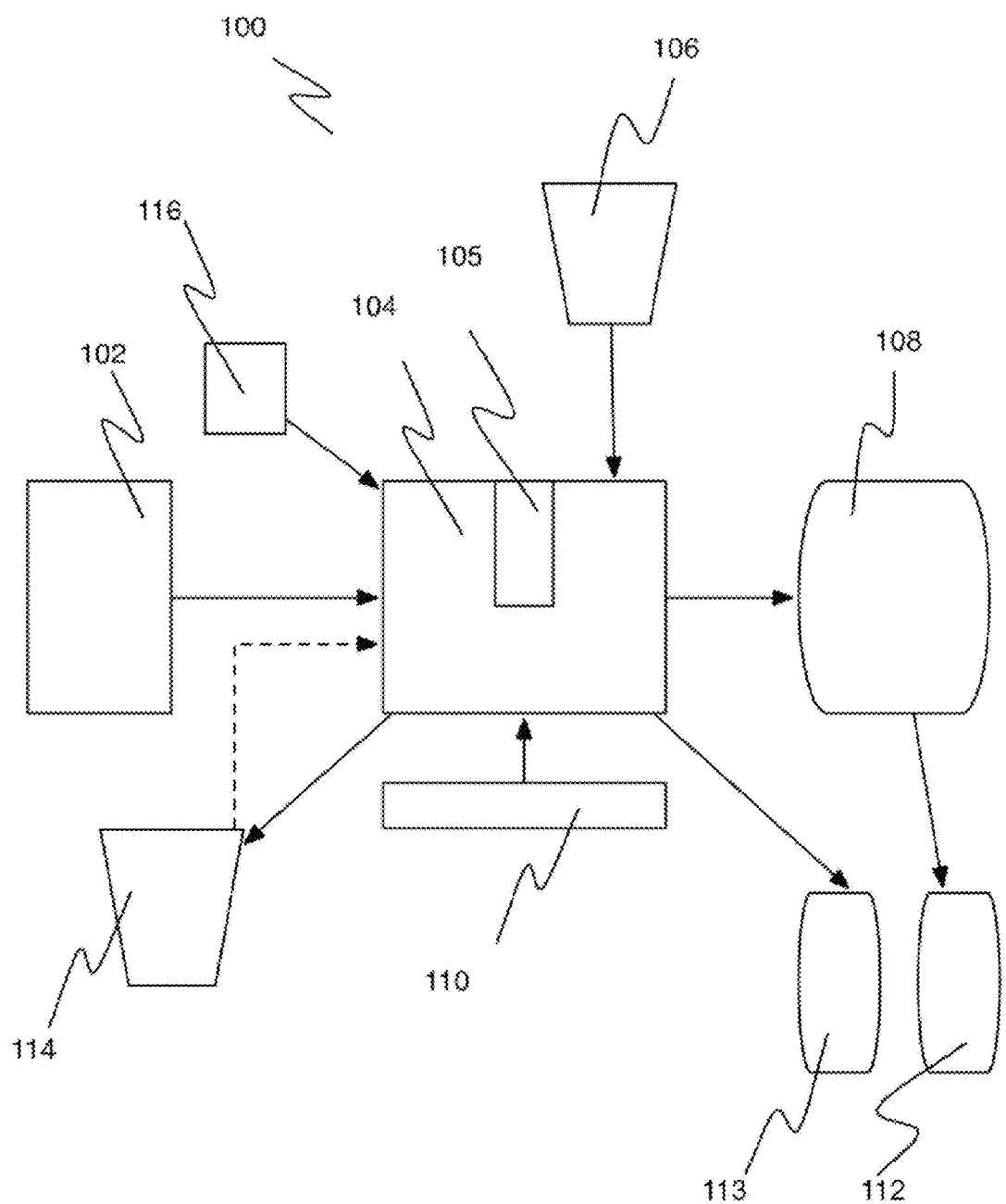
FIG. 6 illustrates an example of an ammonification process of slaughterhouse by-products in the Discussion Section, hereinbelow.

An example environment 100 of an ammonification process of slaughterhouse by-products/waste is shown in FIG. 6. The organic material (by-products) is stored in a container 106. The waste in the container 106 is fed to a bioreactor 104. Water is added to the bioreactor 104 from a water source 102. Inoculum is added to the bioreactor 104 from a source 116. The type of inoculum is selected from group of H1, C1, P1, S1 and A1. Preferably inoculum is from mixed population of S1. The bioreactor can have mixing/stirring means 105 and heating/temperature controlling means 110. According to embodiments heating element 110 is used to heat content of the bioreactor 104 to about 50 degrees of Celsius (40-55 degrees of Celsius for the population S1). If needed, pH can be controlled by adding base (such as NaOH) to the bioreactor 104 to keep pH in levels of over 6. Fermentation time is preferably about 16-48 hours.

During the fermentation process using a mixed bacterial population ammonium/ammonia is released to the fermentation liquid. Samples of the liquid from the bioreactor 104 can be taken from time to time to follow the progress of the process. A parameter to follow is the ammonia/ammonium concentration within the liquid. For example, in certain embodiments of the invention, the fermentation process is complete or sufficient when the change of the concentration ammonia/ammonium between two consecutive samples does not demonstrate a significant increase.

All or some of the liquid from the bioreactor 104 can be led to stripping phase 108 where ammonium/ammonia is extracted as ammonia ($NH_3$) from the liquid. The ammonia can be stored in a container 112 for future use such as a part of fertilizer production. Alternatively some or all of the liquid can be led to container 113 and used directly as fertilizer.

After removing all or some of the liquid the remaining solids and/or liquids can be collected in storage 114 for future use. Some of the material in 114 can be also fed back to bioreactor 104 and used as inoculum for next batch. Additionally some of the liquids and/or solids can be left in the bioreactor 104 to form basis for next batch.

Ammonification of plant materials with high carbohydrate contents might be inhibited by acidification of the medium during the fermentation process. Acidification of media can be avoided with addition of base (such as NaOH) in the culture. Also if plant and animal materials are mixed in appropriate proportions, acidification can be avoided and higher ammonia yields are achieved.

Ammonification of different proteinacious materials can be optimized by selection of appropriate mixed bacteria population. As represented in TABLE 3, ammonification efficiency of each material is dependent on the bacteria population used. E.g. porcine/bovine by-products are ammonified most efficiently using population H1, whereas fish by-products are ammonified most efficiently using the S1 population. On average, populations H1 and S1 are the most efficient ammonifiers on all the different proteinacious materials, and either H1 or S1 could also be selected as a population to be used on ammonification of any material.

S1 and other MBM-derived populations are efficient in ammonification of various animal-origin materials. Some of these materials can give rise to efficiently ammonifying innate populations when incubated under similar conditions used for creating the MBM-derived populations. However, all animal-origin materials do not possess an ammonifying population. Rumen is a well-known source of hyper-ammonia-producing bacterial species, but enrichment of a mixed population capable of ammonification with similar efficiency to MBM-derived populations was not possible. Soil samples also gave rise to efficient and inefficient ammonifying populations depending on the conditions used.

Temperatures from 30° C. to 60° C., more exactly 37-55° C. and pH 5-11, more exactly pH 6-9, were the best for bacterial ammonification with the populations described here. In particular, inoculating organic material with bacterial population substantially similar to S1 results in good ammonification yields. In addition or alternatively, contacting organic material with bacterial population consisting by 53-91% of total population of *Sporanaerobacter acetigenes* and by 8-34% of *Clostridium* spp. results in good ammonification yields. Ammonification works in anaerobic, microaerobic, and aerobic conditions using the mixed populations.

INCORPORATION BY REFERENCE

Numerous references are cited throughout this application, each of which is incorporated by reference herein in its entirety.

CLAIM OF BENEFIT

This application claims the benefit of U.S. Provisional Application Ser. No. 61/789,062, filed on Mar. 15, 2013, the contents of which are incorporated herein by reference in their entirety.

DEPOSIT STATEMENT

Cultures of the following biological material(s) have been deposited with the following international depository:
Centraalbureau voor Schimmelcultures (CBS)
Uppsalalaan 8
3584 CT Utrecht
The Netherlands
under conditions that satisfy the requirements of the Budapest Treaty on the International Recognition of the Deposit of Microorganisms for the Purposes of Patent Procedure.

International Depository Accession

| Mixed Bacterial Population Deposited | CBS Accession No. | Date of Deposit |
|---|---|---|
| S1 | CBS 136063 | Aug. 22, 2013 |

REFERENCES

Chen, G. J., Russell, J. B. 1989. More monensin-sensitive, ammonia-producing bacteria from the rumen. *Appl. Environ. Microbiol.* 55, 1052-1057.

Dowd, S. E., Wolcott, R. D., Sun, Y., McKeehan, T., Smith, E., Rhoads, D. 2008a. Polymicrobial nature of chronic diabetic foot ulcer biofilm infections determined using bacterial tag encoded FLX amplicon pyrosequencing (bTEFAP). *PLoS ONE* 3(10): e3326.

Dowd, S. F., Sun, Y., Secor, P. R., Rhoads, D. D., Wolcott, B. M., James, G. A., Wolcott, R. D. 2008b. Survey of bacterial diversity in chronic wounds using Pyrosequencing, DGGE, and full ribosome shotgun sequencing. *BMC Microbiology* 8: 43.

EC. 2009. Regulation (EC) No 1069/2009 of the European Parliament and of the Council of 21 Oct. 2009 laying down health rules as regards animal by-products and derived products not intended for human consumption and repealing Regulation (EC) No 1774/2002 (Animal by-products Regulation). *Off. J. Eur. Union* L300: 1-33.

Eschenlauer, S. C. P., McKain, N., Walker, N. D., McEwan, N. R., Newbold, C. J., Wallace, R. J. 2002. Ammonia production by ruminal microorganisms and enumeration, isolation, and characterization of bacteria capable of growth on peptides and amino acids from the sheep rumen. *Appl. Environ. Microbiol.* 68(10): 4925-4931.

EU. 2011. Commission regulation (EU) No 142/2011 of 25 Feb. 2011 implementing Regulation (EC) No 1069/2009 of the European Parliament and of the Council laying down health rules as regards animal by-products and derived products not intended for human consumption and implementing Council Directive 97/78/EC as regards certain samples and items exempt from veterinary checks at the border under that Directive. *Off J. Eur. Union* L54: 1-354.

Fouts, D. E., Szpakowski, S., Purushe, J., Torralba, M., Waterman, R. C., MacNeil, M. D., Alexander, L. J., Nelson, K. E. 2012. Next generation sequencing to define prokaryotic and fungal diversity in the bovine rumen. *PLoS One* 7(11): e48289.

Krause, D. O., Russell, J. B. 1996. An rRNA approach for assessing the role of obligate amino acid-fermenting bacteria in ruminal amino acid deamination. *Appl. Environ. Microbiol.* 62, 815-821.

Russell, J. B., Strobel, H. J., Chen, G. J. 1988. Enrichment and isolation of a ruminal bacterium with a very high specific activity of ammonia production. *Appl. Environ. Microbiol.* 54, 872-877.

Wolcott, R., Gontcharova, V., Sun, Y., Dowd, S. E. 2009. Evaluation of the bacterial diversity among and within individual venous leg ulcers using bacterial tag-encoded FLX and Titanium amplicon pyrosequencing and metagenomic approaches. *BMC Microbiology* 9: 226.

We claim:

1. A process for producing ammonia or ammonium from an organic material, comprising:
    fermenting an aqueous medium comprising organic material in the presence of a mixed bacterial population capable of ammonification, in a bioreactor, wherein the fermenting is under conditions, and for a sufficient period of time, to produce a fermentation product that comprises ammonia or ammonium;
    wherein the organic material comprises nitrogenous compounds suitable for conversion to ammonia or ammonium and
    wherein the mixed bacterial population is substantially similar to an isolated mixed bacterial population of S1 (CBS Accession No. 136063), wherein the substantially similar mixed bacterial population has a correlation coefficient of at least 0.90, relative to S1.

2. The process of claim 1 wherein the fermenting is conducted at a temperature ranging between 30-60 degrees of Celsius and at a pH ranging from about 5 to about 11.

3. The process of claim 1 wherein the fermenting is conducted at a temperature ranging between 40-50 degrees of Celsius and at a pH ranging from about 6 to about 9.

4. The process of claim 1, wherein the substantially similar mixed bacterial population has a correlation coefficient of at least 0.95 relative to the isolated mixed bacterial population of S1 (CBS Accession No. 136063).

5. The process of claim 1 wherein the fermenting is conducted at a temperature ranging from about 40° C. to about 55° C.

6. The process of claim 1, further comprising recovering ammonia or ammonium from the fermentation product.

7. The process of claim 6, wherein the ammonia or ammonium is recovered mechanically or is precipitated.

8. The process of claim 6, wherein the ammonia or ammonium is recovered by the steps of:

(a) separating solid and liquid fermentation products;
    (b) collecting the liquid fermentation product comprising ammonia or ammonium-water or collecting a gas mixture released during the fermenting process or during separating step (a); and
    (c) recovering the ammonia or ammonium.

9. The process of claim 1, wherein the nitrogenous compounds are amines or proteins.

10. The process of claim 1 wherein the organic material is selected from the group consisting of meat-and bone meal (MBM), animal meals, animal by-products, slaughterhouse waste, whey, municipal waste, fish meal, food and fermentation industry waste streams and combinations thereof.

11. The process of claim 10 wherein the food industry waste is selected from the group consisting of animal by-products, animal meals and food waste.

12. The process of claim 1 wherein the fermenting is conducted under anaerobic conditions.

* * * * *

SEQUENCE LISTING

```
<160> NUMBER OF SEQ ID NOS: 2

<210> SEQ ID NO 1
<211> LENGTH: 19
<212> TYPE: DNA
<213> ORGANISM: Artificial
<220> FEATURE:
<223> OTHER INFORMATION: Universal 16S RNA Bacteria Primer
<220> FEATURE:
<221> NAME/KEY: misc_feature
<222> LOCATION: (11)..(11)
<223> OTHER INFORMATION: n is a, c, g, or t

<400> SEQUENCE: 1
gagtttgatc ntggctcag                                              19

<210> SEQ ID NO 2
<211> LENGTH: 18
<212> TYPE: DNA
<213> ORGANISM: Artificial
<220> FEATURE:
<223> OTHER INFORMATION: Universal 16S RNA Bacteria Primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (14)..(14)
<223> OTHER INFORMATION: k is t or g

<400> SEQUENCE: 2
gtnttacngc ggckgctg                                               18
```